United States Patent
Ehata

(10) Patent No.: US 7,199,591 B2
(45) Date of Patent: Apr. 3, 2007

(54) METHOD OF MEASURING RELATIVE DIELECTRIC CONSTANT OF DIELECTRIC SUBSTANCE OF POWDERS, CAVITY RESONATOR USED IN THE SAME, AND APPLICATION APPARATUS

(75) Inventor: Katsufumi Ehata, Tokyo (JP)

(73) Assignee: TDK Corporation, Tokyo (JP)

( * ) Notice: Subject to any disclaimer, the term of this patent is extended or adjusted under 35 U.S.C. 154(b) by 33 days.

(21) Appl. No.: 10/942,900

(22) Filed: Sep. 17, 2004

(65) Prior Publication Data

US 2005/0093555 A1    May 5, 2005

(30) Foreign Application Priority Data

| Oct. 31, 2003 | (JP) | ............................. 2003-372581 |
| Nov. 5, 2003 | (JP) | ............................. 2003-375478 |
| Mar. 18, 2004 | (JP) | ............................. 2004-078519 |

(51) Int. Cl.
*G01R 27/04* (2006.01)

(52) U.S. Cl. ...................................... 324/636; 324/633

(58) Field of Classification Search ................. 324/636
See application file for complete search history.

(56) References Cited

U.S. PATENT DOCUMENTS

| 4,891,573 | A | | 1/1990 | Kent | |
| 5,260,665 | A | * | 11/1993 | Goldberg et al. | ............ 324/636 |
| 5,420,100 | A | * | 5/1995 | Vittoria et al. | ............... 505/162 |
| 5,455,516 | A | * | 10/1995 | Jean et al. | ................... 324/639 |
| 5,764,538 | A | * | 6/1998 | Cheiky-Zelina | ............... 702/29 |
| 5,861,757 | A | * | 1/1999 | Hougham et al. | .......... 324/672 |
| 5,864,239 | A | * | 1/1999 | Adams et al. | ............... 324/636 |
| 6,025,291 | A | * | 2/2000 | Murakawa | ................... 501/136 |
| 6,147,503 | A | * | 11/2000 | Nelson et al. | ............... 324/637 |
| 6,182,499 | B1 | * | 2/2001 | McFarland et al. | ......... 73/24.06 |
| 6,407,555 | B2 | * | 6/2002 | Joshi et al. | ................. 324/636 |
| 6,452,404 | B2 | * | 9/2002 | Moeller et al. | ............. 324/633 |
| 6,586,946 | B2 | * | 7/2003 | Hefti et al. | .................. 324/636 |
| 6,771,080 | B2 | * | 8/2004 | Conrads et al. | ............. 324/636 |
| 2002/0149377 | A1 | * | 10/2002 | Hefti et al. | .................. 324/636 |

FOREIGN PATENT DOCUMENTS

| JP | 6-138075 | 5/1994 |
| JP | 9-311151 | 12/1997 |

OTHER PUBLICATIONS

F. T. Ulaby, et al., "Microwave Probe for in Situ Observations of Vegetation Dielectric", Instrumentation and Measurement Technology Conference, vol. CONF. 8, XP-010037037, May 14, 1991, pp. 631-635.

Yonghong Hua, et al., "A Mixture Approach with Perturbation Technique for Microwave Characterization of Conducting Polymers", Electrical and Computer Engineering, XP-010193724, Sep. 5, 1995, pp. 501-504.

Weiguo Xi, et al., "Field Analysis of New Coaxial Dielectrometer", IEEE Transactions on Microwave Theory and Techniques, vol. 40, No. 10, XP-000307040, Oct. 1, 1992, pp. 1927-1934.

Stuart O. Nelson, et al., "Sensing Pulverized Material Mixture Proportions by Resonant Cavity Measurements", IEEE Transactions on instrumentation and measurement, vol. 47, No. 5, XP-000862430, Oct. 1998, pp. 1201-1204.

* cited by examiner

*Primary Examiner*—Andrew H. Hirshfeld
*Assistant Examiner*—Marina Kramskaya
(74) *Attorney, Agent, or Firm*—Oblon, Spivak, McClelland, Maier & Neustadt, P.C.

(57) ABSTRACT

A relative dielectric constant of a mixed substance consisting of powders and a liquid medium is calculated, and then the relative dielectric constant of the mixed substance or a relative dielectric constant of the liquid medium is calculated as a relative dielectric constant of the powders where the relative dielectric constant of the mixed substance becomes equal to a relative dielectric constant of the liquid medium. Therefore, the relative dielectric constant of the powders can be measured with high precision even in a high-frequency band in excess of several GHz.

6 Claims, 18 Drawing Sheets

FIG. 20

ANALYSIS OF ELECTRIC FILED IN CYLINDRICAL CAVITY RESONATOR

IDEAL CYLINDRICAL CAVITY RESONATOR

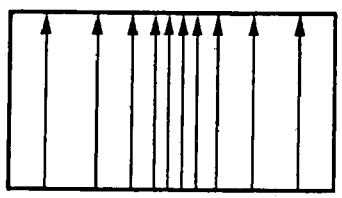

ELECTRIC FIELD ARE CONCENTRATED AT CENTER PORTION (a)

CYLINDRICAL CAVITY RESONATOR WITH OPENING PORTIONS

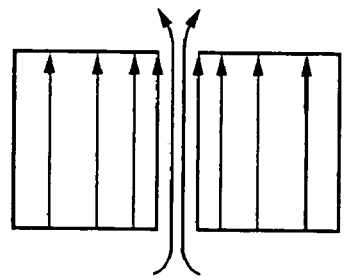

LEAKAGE OF ELECTRIC FIELD (b)

CYLINDRICAL CAVITY RESONATOR WITH OPENING PORTIONS IN WHICH SUPPORTER IS PROVIDED

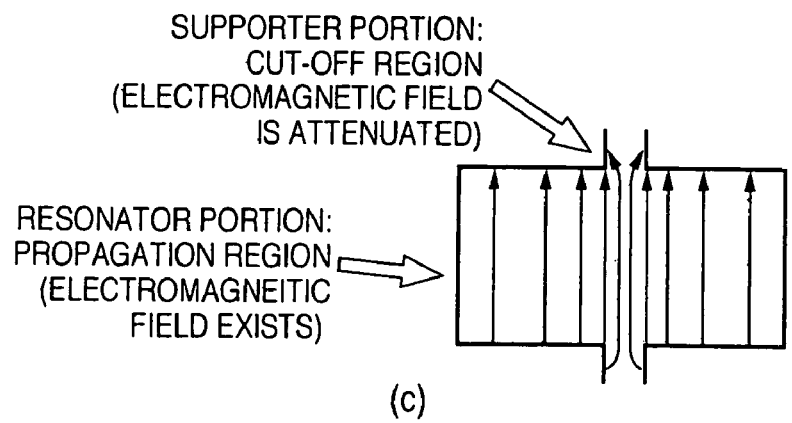

SUPPORTER PORTION: CUT-OFF REGION (ELECTROMAGNETIC FIELD IS ATTENUATED)

RESONATOR PORTION: PROPAGATION REGION (ELECTROMAGNEITIC FIELD EXISTS)

(c)

TOP VIEW OF SUPPORTER

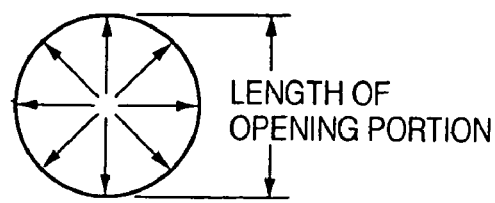

LENGTH OF OPENING PORTION (d)

FIG. 24
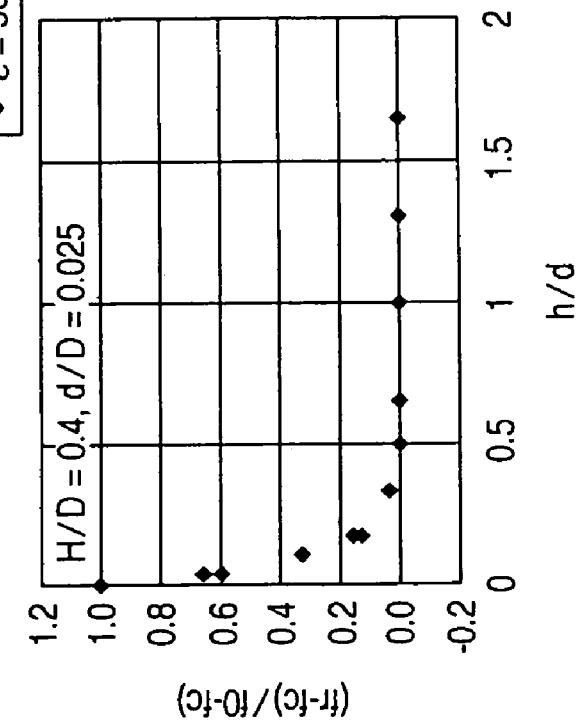
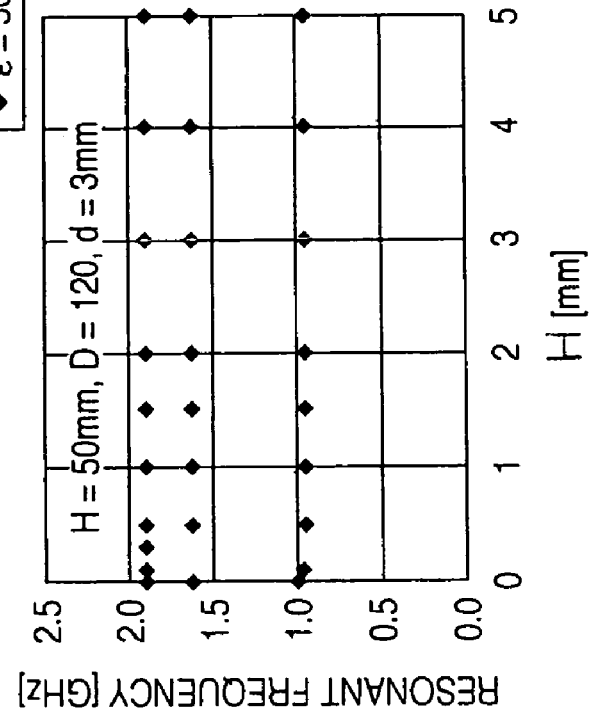

METHOD OF MEASURING RELATIVE DIELECTRIC CONSTANT OF DIELECTRIC SUBSTANCE OF POWDERS, CAVITY RESONATOR USED IN THE SAME, AND APPLICATION APPARATUS

BACKGROUND OF THE INVENTION

The present invention relates to a method of measuring a relative dielectric constant of a dielectric substance of powders and, more particularly, a method of measuring a relative dielectric constant of powders capable of measuring a relative dielectric constant of a dielectric substance of powders with high precision even in a high-frequency band in excess of several GHz.

With improvements in the performance of various radio equipments, high-frequency ceramics dielectric substances of higher performance are requested. Normally the ceramics dielectric substances are used in the form of sintered products that are obtained by sintering the powder dielectric substance. Also, the composite dielectric substance in which the powder dielectric substance and the resin, or the like are mixed in various ratios is employed as the circuit parts. As a result, upon developing the high-frequency ceramics dielectric substance, it is necessary and indispensable to measure a relative dielectric constant of the dielectric substance in its powder state as the dielectric property of such dielectric substance.

For example, as disclosed in Japanese Patent No. 3127623, and the like, powders whose relative dielectric constant is to be measured are sealed in the vessel in which a pair of electrodes are arranged to oppose to each other at a predetermined interval, and then the relative dielectric constant of the powders is measured. Then, the relative dielectric constant of a mixed substance consisting of the powders and a liquid is measured by applying a voltage between a pair of electrodes, and then the relative dielectric constant of the powders is calculated based on the measured relative dielectric constant of the mixed substance.

However, in the method of measuring the relative dielectric constant of the powders in the prior art, the presence of the stray capacitance and the stray reactance cannot be ignored when the relative dielectric constant of the powders is to be measured in the high-frequency band in excess of several GHz. As a result, such a problem existed that the resonation of the overall measuring system is caused and thus it is unfeasible to measure the relative dielectric constant of the powders with high precision.

SUMMARY OF THE INVENTION

Therefore, it is an object of the present invention to provide a method of measuring a relative dielectric constant of powders, capable of measuring a relative dielectric constant of powders with high precision even in a high-frequency band in excess of several GHz.

Such object of the present invention is attained by providing a method of measuring a relative dielectric constant of powders comprising the steps of calculating a relative dielectric constant of a mixed substance consisting of powders and a liquid medium, and then calculating the relative dielectric constant of the mixed substance or a relative dielectric constant of the liquid medium as the relative dielectric constant of the powders when the relative dielectric constant of the mixed substance becomes equal to the relative dielectric constant of the liquid medium.

Also, the object of the present invention is attained by providing a method of measuring a relative dielectric constant of powders comprising the steps of sealing a mixed substance consisting of the powders and a liquid medium in a resonator, then inputting an electromagnetic wave into the resonator, then calculating a relative dielectric constant of the mixed substance based on a response of the electromagnetic wave, and then calculating a relative dielectric constant of the powders from the relative dielectric constant of the mixed substance and a relative dielectric constant of the liquid medium.

Also, the object of the present invention is attained by providing a method of measuring a relative dielectric constant of powders comprising the steps of inputting an electromagnetic wave into a vessel in which a mixed substance consisting of the powders and a liquid medium is filled, then calculating a relative dielectric constant of the mixed substance based on a response of the electromagnetic wave, and then calculating a relative dielectric constant of the powders from the relative dielectric constant of the mixed substance and a relative dielectric constant of the liquid medium.

In the preferred embodiment of the present invention, calculation of the relative dielectric constant of powders is executed by calculating the relative dielectric constant of the mixed substance or the relative dielectric constant of the liquid medium as the relative dielectric constant of the powders when the relative dielectric constant of the mixed substance becomes equal to the relative dielectric constant of the liquid medium.

A procedure of detecting a point of time when the relative dielectric constant of the mixed substance becomes equal to the relative dielectric constant of the liquid medium is executed by measuring the relative dielectric constant of the mixed substance while changing gradually the relative dielectric constant of the liquid medium.

In the preferred embodiment of the present invention, the liquid medium contains a liquid, or a liquid and a powder dielectric substance, or a liquid, a powder dielectric substance, and a dispersing agent.

The object of the present invention is attained by providing a method of measuring a relative dielectric constant of powders which comprises the steps of sealing a mixed substance consisting of powders and a liquid medium in a resonator, then inputting an electromagnetic wave into the resonator, then calculating a relative dielectric constant of the mixed substance based on a response of the electromagnetic wave, and then calculating a relative dielectric constant of the powders from the calculated relative dielectric constant of the mixed substance and a volume ratio of the powders in the mixed substance.

Also, the object of the present invention is attained by providing a method of measuring a relative dielectric constant of powders which comprises the steps of inputting an electromagnetic wave into a vessel in which a mixed substance consisting of powders and a liquid medium is filled, then calculating a relative dielectric constant of the mixed substance based on a response of the electromagnetic wave, and then calculating a relative dielectric constant of the powders from the calculated relative dielectric constant of the mixed substance and a volume ratio of the powders in the mixed substance.

In the preferred embodiment of the present invention, the relative dielectric constant of the liquid medium is 0.5 times or more the relative dielectric constant of a powder composition.

In the preferred embodiment of the present invention, the relative dielectric constant of the liquid medium is 0.5 times to 2.0 times the relative dielectric constant of a powder composition.

In the preferred embodiment of the present invention, the liquid medium contains a liquid, or a liquid and a powder dielectric substance, or a liquid, a powder dielectric substance, and a dispersing agent.

In the preferred embodiment of the present invention, calculation of the relative dielectric constant of powders is executed by using the logarithmic mixture rule or the Lichtenecker-Rother's Formula.

A cavity resonator in which at least one opening portion into which a measured dielectric substance is inserted is formed in a center portion of the cavity resonator in an axis direction and also a supporter is formed on an outside of the opening portion, wherein a relationship h/d between a length d of the opening portion and a length h of the supporter is set to 0.5 or more. Thus, leakage of the electromagnetic wave from the resonator can be suppressed.

A cavity resonator which is used in a method of measuring a relative dielectric constant of powders that comprises the steps of sealing a mixed substance consisting of powders and a liquid medium in a resonator, then inputting an electromagnetic wave into the resonator, then calculating a relative dielectric constant of the mixed substance based on a response of the electromagnetic wave, and then calculating a relative dielectric constant of the powders from the relative dielectric constant of the mixed substance and a relative dielectric constant of the liquid medium, and in which at least one opening portion into which a measured dielectric substance is inserted is formed in the cavity resonator and also a supporter is formed on an outside of the opening portion, wherein a relationship h/d between a length d of the opening portion and a length h of the supporter is set to 0.5 or more. Thus, the cut-off structure can be obtained by preventing the leakage of the electromagnetic wave from the opening portion of the resonator.

A cavity resonator which is used in a method of measuring a relative dielectric constant of powders comprising the steps of sealing a mixed substance consisting of powders and a liquid medium in a resonator, then inputting an electromagnetic wave into the resonator, then calculating a relative dielectric constant of the mixed substance based on a response of the electromagnetic wave, and then calculating a relative dielectric constant of the powders from the calculated relative dielectric constant of the mixed substance and a volume ratio of the powders in the mixed substance, and in which at least one opening portion into which a measured dielectric substance is inserted is formed in the cavity resonator and also a supporter is formed on an outside of the opening portion, wherein a relationship h/d between a length d of the opening portion and a length h of the supporter is set to 0.5 or more. Thus, the cut-off structure can be obtained by preventing the leakage of the electromagnetic wave from the opening portion of the resonator, and the resonant frequency and the unloaded Q value of the resonator can be measured stably.

Also, the dielectric substance measuring system for inserting the rod-like-shaped dielectric substance into the cavity resonator, then measuring the resonant frequency and the unloaded Q value of the cavity resonator, and then measuring the relative dielectric constant and the dielectric loss tangent of the inserted rod-like dielectric substance based on the measured results is implemented.

Also, the resonator or the filter that can attain the intended resonance characteristic by inserting the rod-like-shaped dielectric substance into the cavity resonator is implemented.

According to the first measuring method of the present invention, it is possible to provide a method of measuring a relative dielectric constant of powders, which is able to measure a relative dielectric constant of powders with high precision even in the high-frequency band in excess of several GHz. Also, it is possible to provide a method of measuring a relative dielectric constant of powders, which is able to measure a relative dielectric constant of powders of the high relative dielectric constant with high precision.

Also, according to the second measuring method, it is possible to provide a method of measuring a relative dielectric constant of powders, which is able to prevent degradation of a measuring precision caused when the relative dielectric constant of powders is detected by the extrapolation, by selecting a liquid medium having a value of the relative dielectric constant that is close to a value the relative dielectric constant of the detected powders. In addition, improvement of a measuring precision of the relative dielectric constant of powders can be achieved by calculating the relative dielectric constant of powders by using the logarithmic mixture rule or the Lichtenecker-Rother's Formula.

Also, in the cavity resonator used to measure the relative dielectric constant of powders in the present invention, at least one opening portion into which the measured dielectric substance is inserted is formed in the center portion in the axis direction and also the supporter is formed on the outside of the opening portion. In this cavity resonator, the optimum length of the supporter can be obtained by setting a relationship h/d between the length d of the opening portion and the length h of the supporter to 0.5 or more.

In this case, the cavity resonator is not limited to the application of powders, and can be applied to any measured sample if such measured sample is formed of the dielectric substance.

Also, it is feasible to implement a dielectric substance measuring system that inserts the rod-like-shaped dielectric substance into the cavity resonator, then measures the resonant frequency and the unloaded Q value of the cavity resonator, and then measures the relative dielectric constant and the dielectric loss tangent of the inserted rod-like dielectric substance based on the measured results.

Also, it is feasible to implement the resonator or the filter that can attain the target resonance characteristic by inserting the rod-like-shaped dielectric substance into the cavity resonator.

Figure 16:
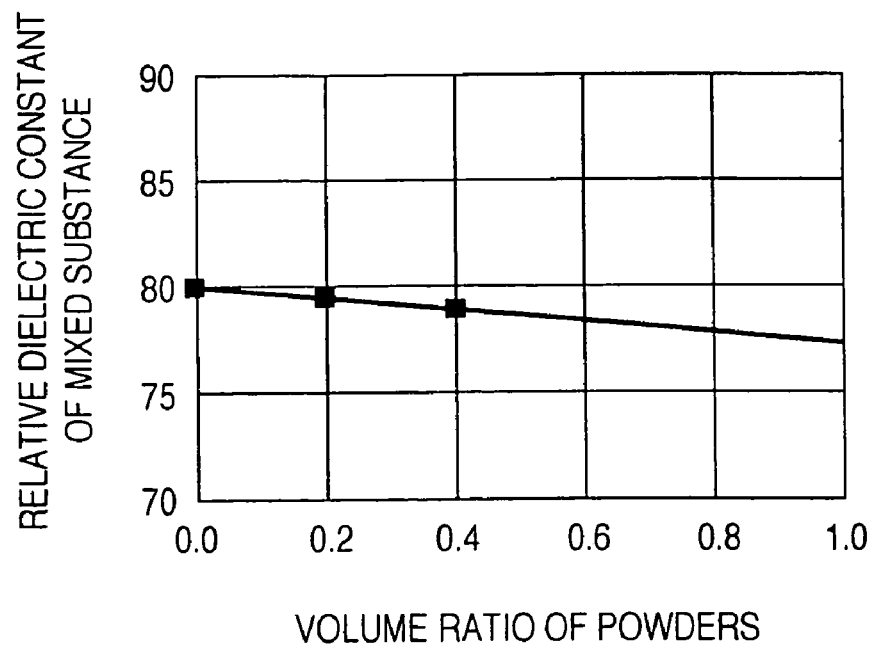

[FIG. 16] FIG. 16 is a graph showing another relationship between the volume ratio of powders and the relative dielectric constant of the mixed substance 18 in Example 5.

Figure 17:
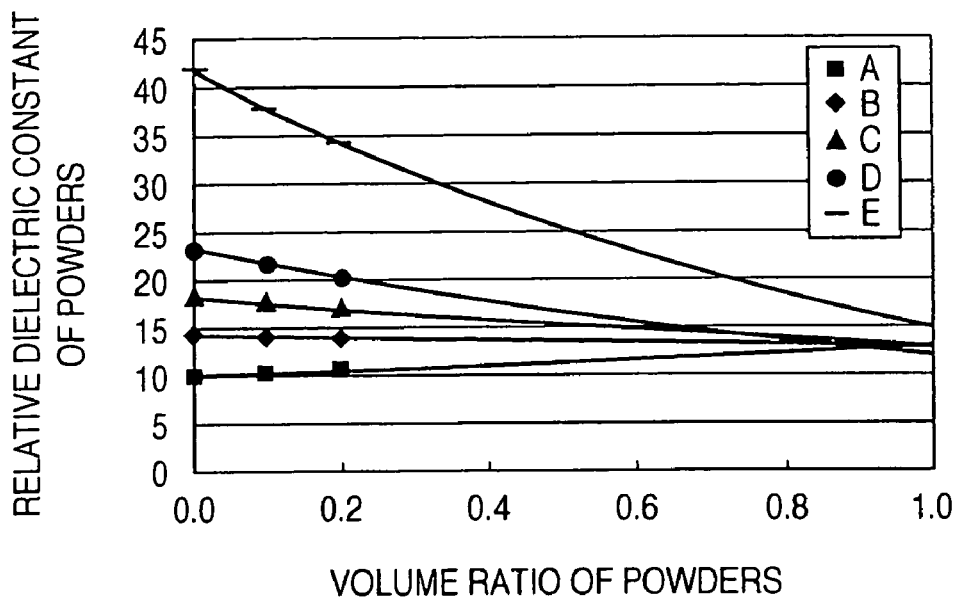

FIG. 17 is a graph showing a relationship between the volume ratio of powders and the relative dielectric constant of the mixed substance 18 in Example 6.

Figure 18:
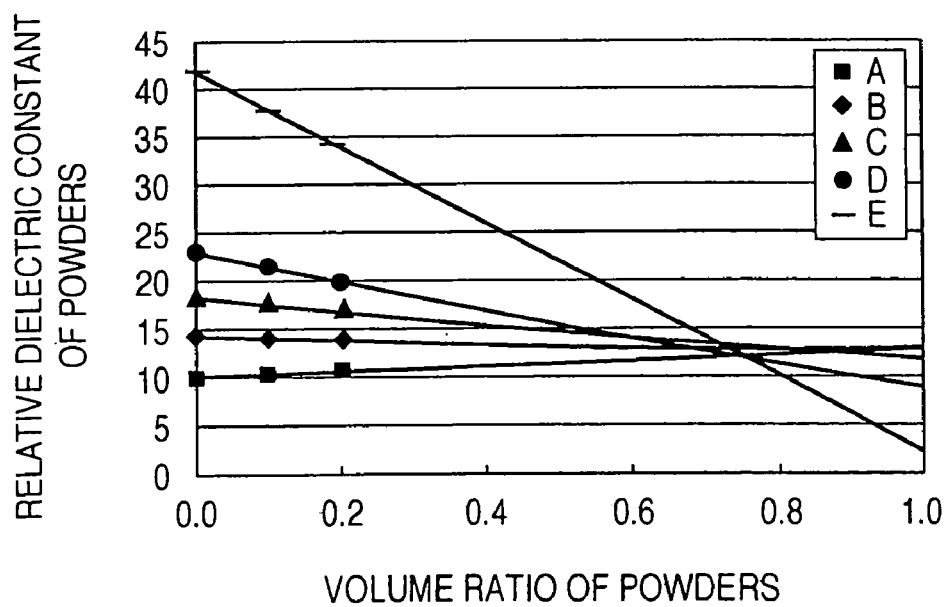

FIG. 18 is a graph showing another relationship between the volume ratio of powders and the relative dielectric constant of the mixed substance 18 in Example 6.

Figure 19:
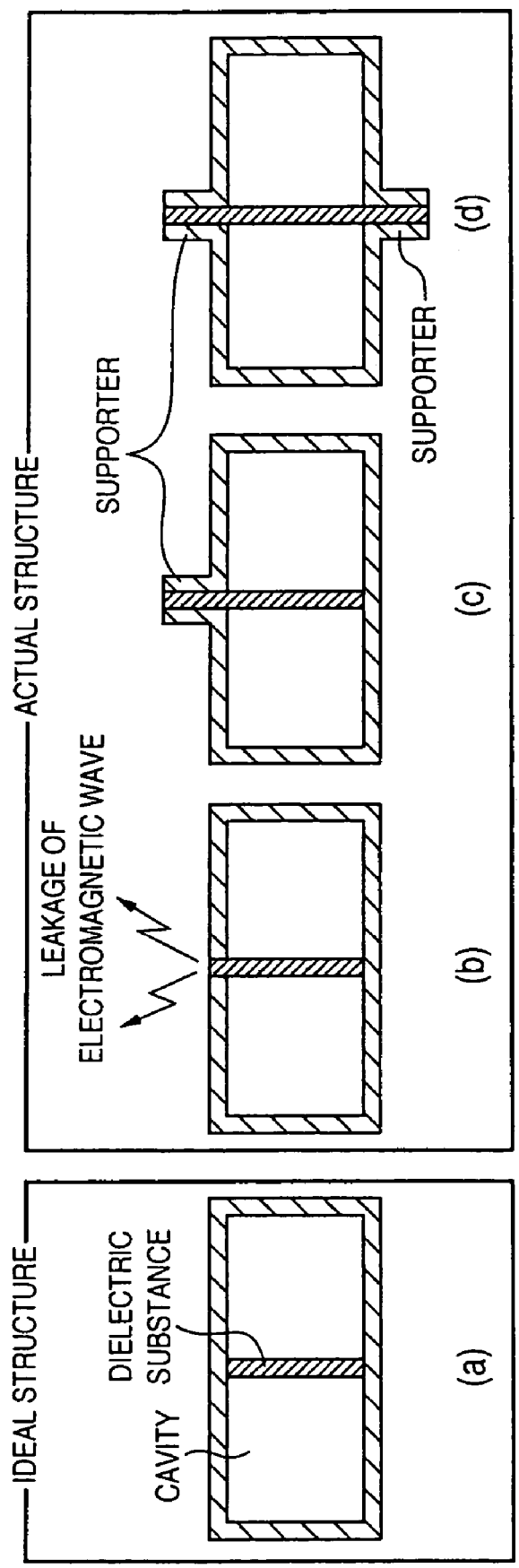

FIG. 19 is a view showing a configuration of a cylindrical cavity resonator used in the measurement of the relative dielectric constant of powders in the present invention.

FIG. 20 is a view explaining a distribution of an electric field in the cylindrical cavity resonator.

Figure 21:
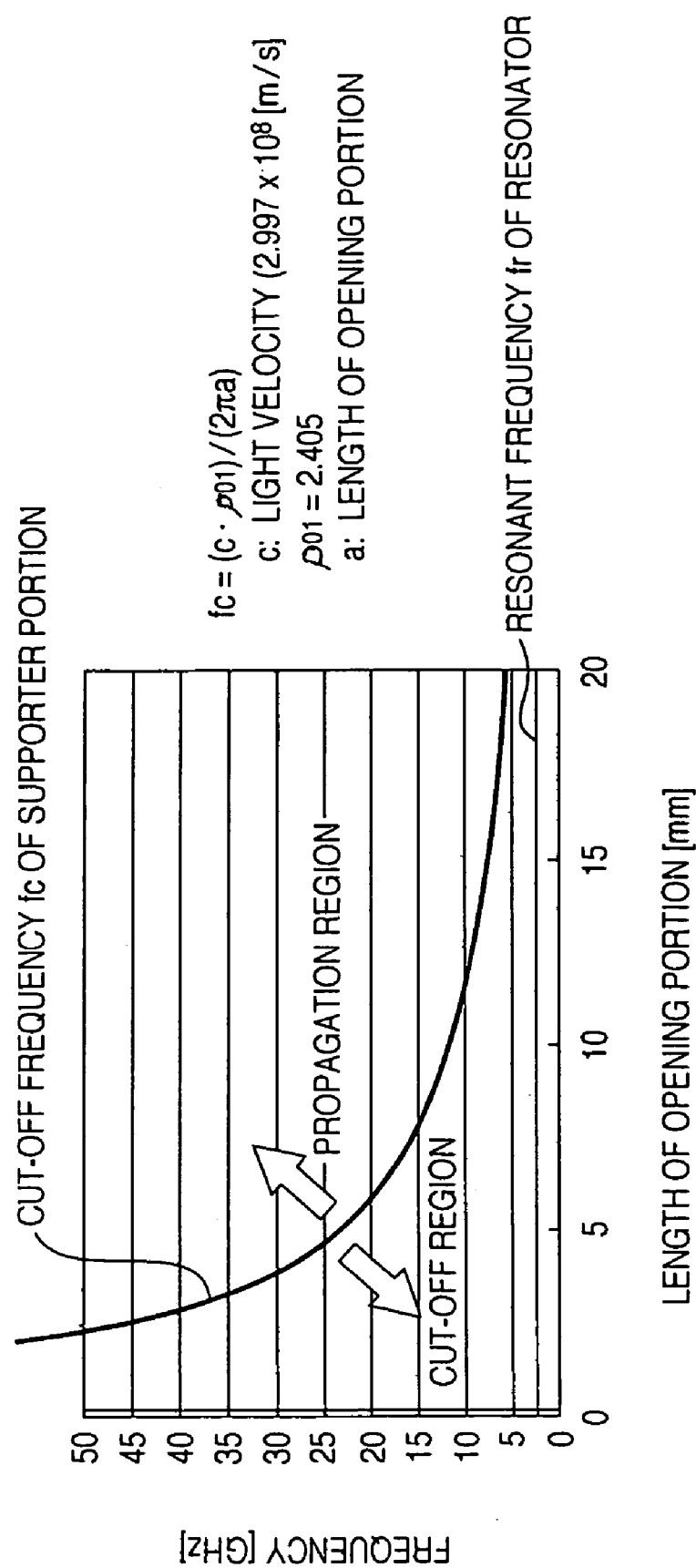

FIG. 21 is a view showing a cut-off frequency of a supporter portion of the cylindrical cavity resonator.

Figure 22:
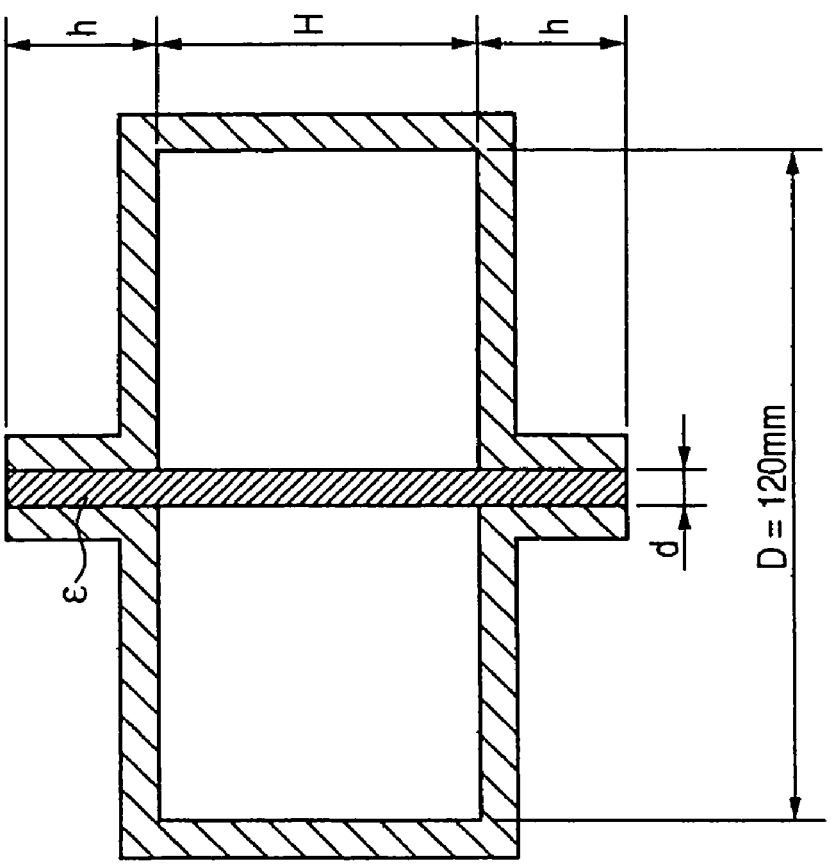

FIG. 22 is a view showing conditions required for a resonator shape to execute a simulation to derive the optimum value of the supporter of the cylindrical cavity resonator.

Figure 23:
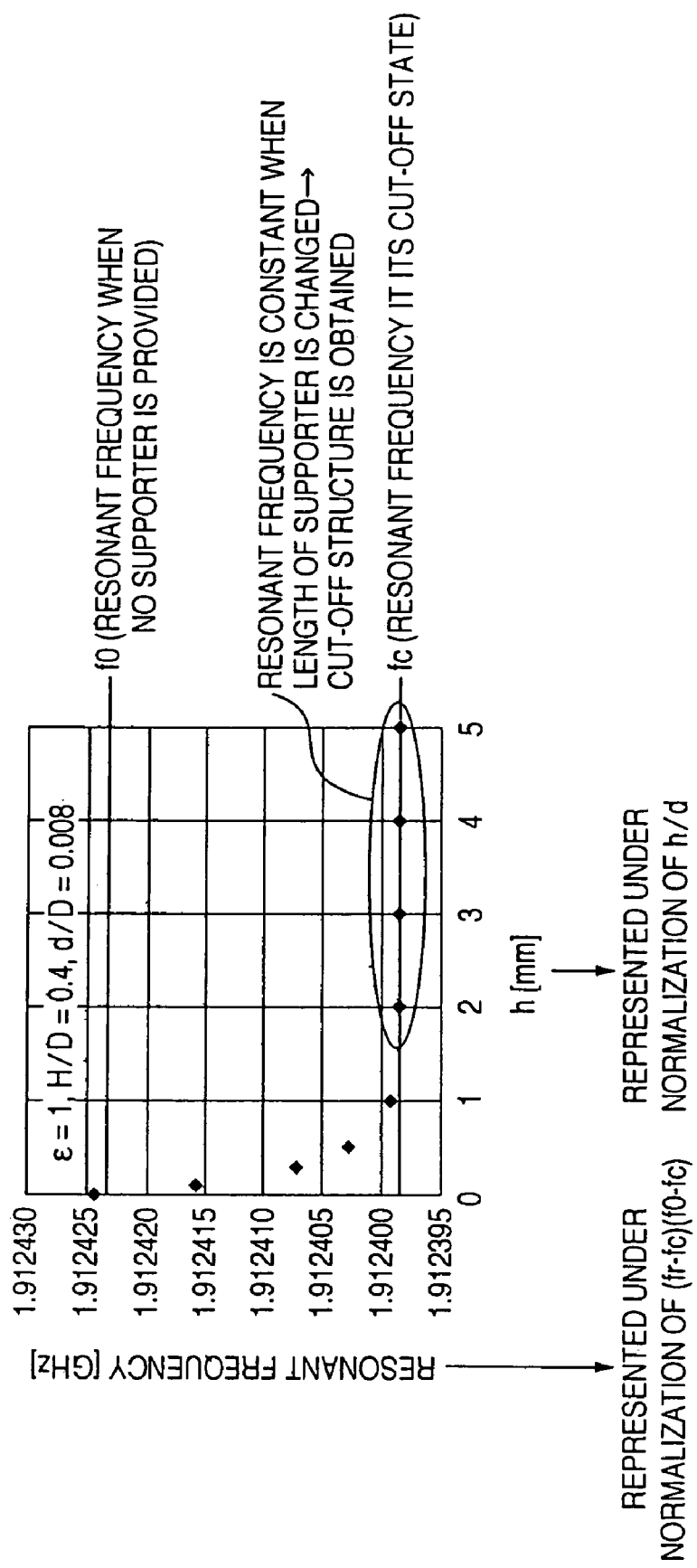

FIG. 23 is a view showing results of the simulation.

FIG. 24 is a view explaining a difference caused due to the relative dielectric constant E of a measured dielectric substance.

Figure 25:
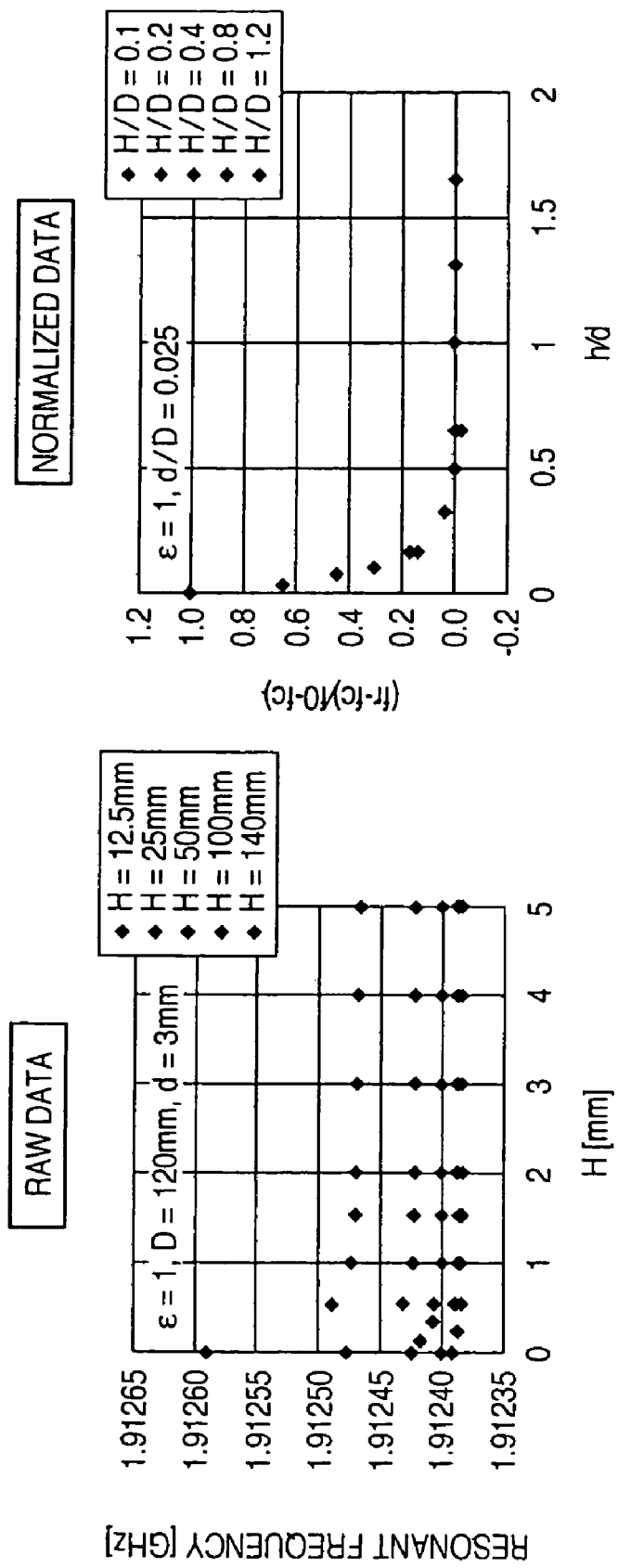

FIG. 25 is a view explaining a difference caused due to a height H of the resonator.

Figure 26:
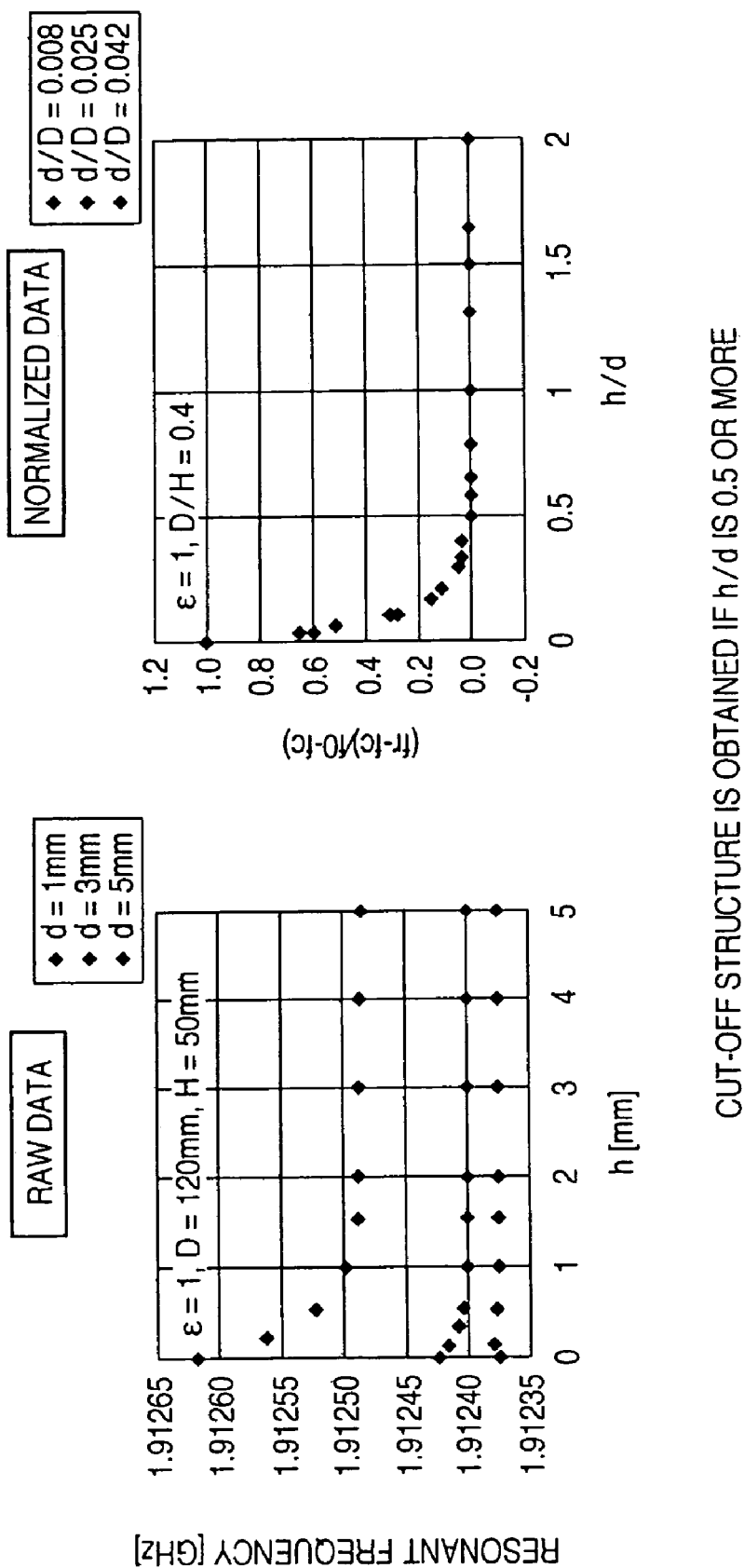

FIG. 26 is a view explaining a difference caused due to a diameter d of an insertion hole of the dielectric substance.

DETAILED DESCRIPTION OF THE PREFERRED EMBODIMENTS

Detailed explanation will hereinafter be made of preferred embodiments of the present invention with reference to the accompanying drawings.

Figure 1:
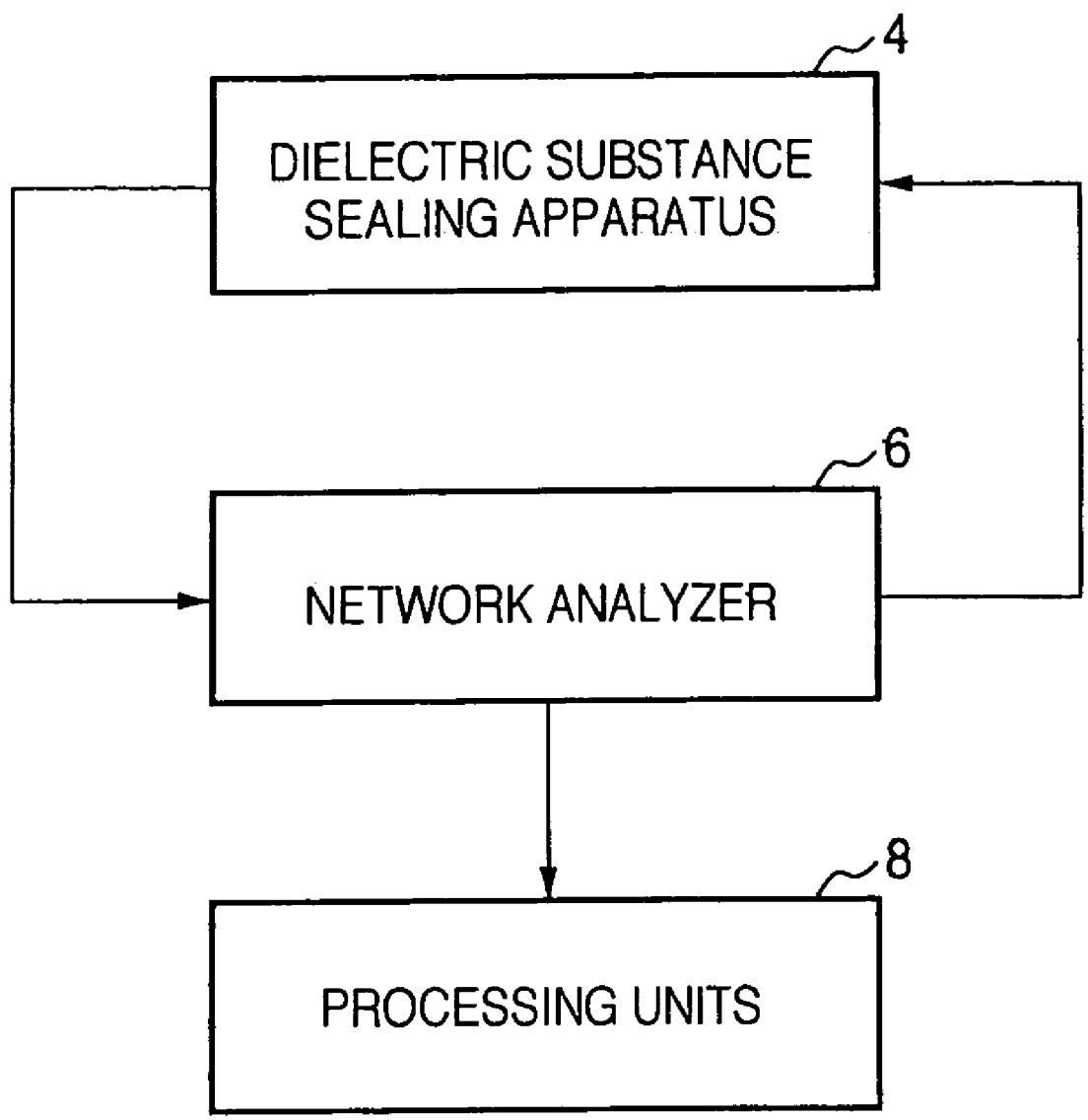
FIG. 1 is a block diagram of a measuring system for executing a method of measuring a relative dielectric constant of powders according to preferred embodiments of the present invention.

FIG. 1 is a block diagram of a measuring system for implementing a method of measuring a relative dielectric constant of powders according to preferred embodiments of the present invention.

As shown in FIG. 1, a measuring system 2 includes a dielectric substance sealing apparatus 4, a network analyzer 6, and a processing unit 8.

The dielectric substance sealing apparatus 4 is an apparatus in which a mixed substance consisting of powders whose relative dielectric constant is to be measured and a liquid medium is sealed.

The network analyzer 6 is constructed to input the electromagnetic wave into the dielectric substance sealing apparatus 4 and output to the processing unit 8 the measured result of the electromagnetic wave that is output from the dielectric substance sealing apparatus 4 in response to the input of the electromagnetic wave.

The processing unit 8 is constructed to calculate the relative dielectric constant of the powders based on the measured result that is output from the network analyzer 6.

Figure 2:
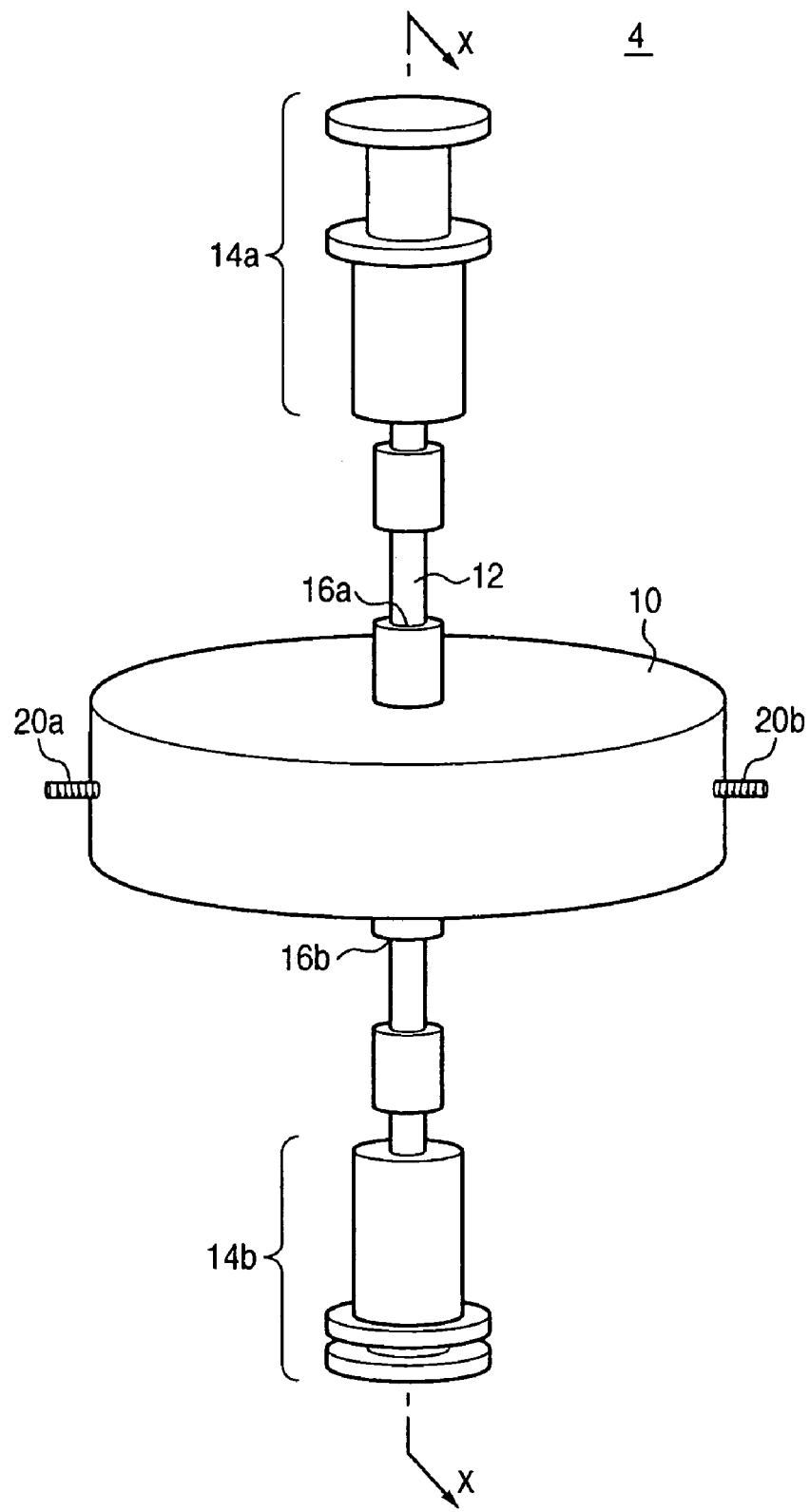
FIG. 2 is a schematic perspective view of a dielectric substance sealing apparatus 4.
Figure 3:
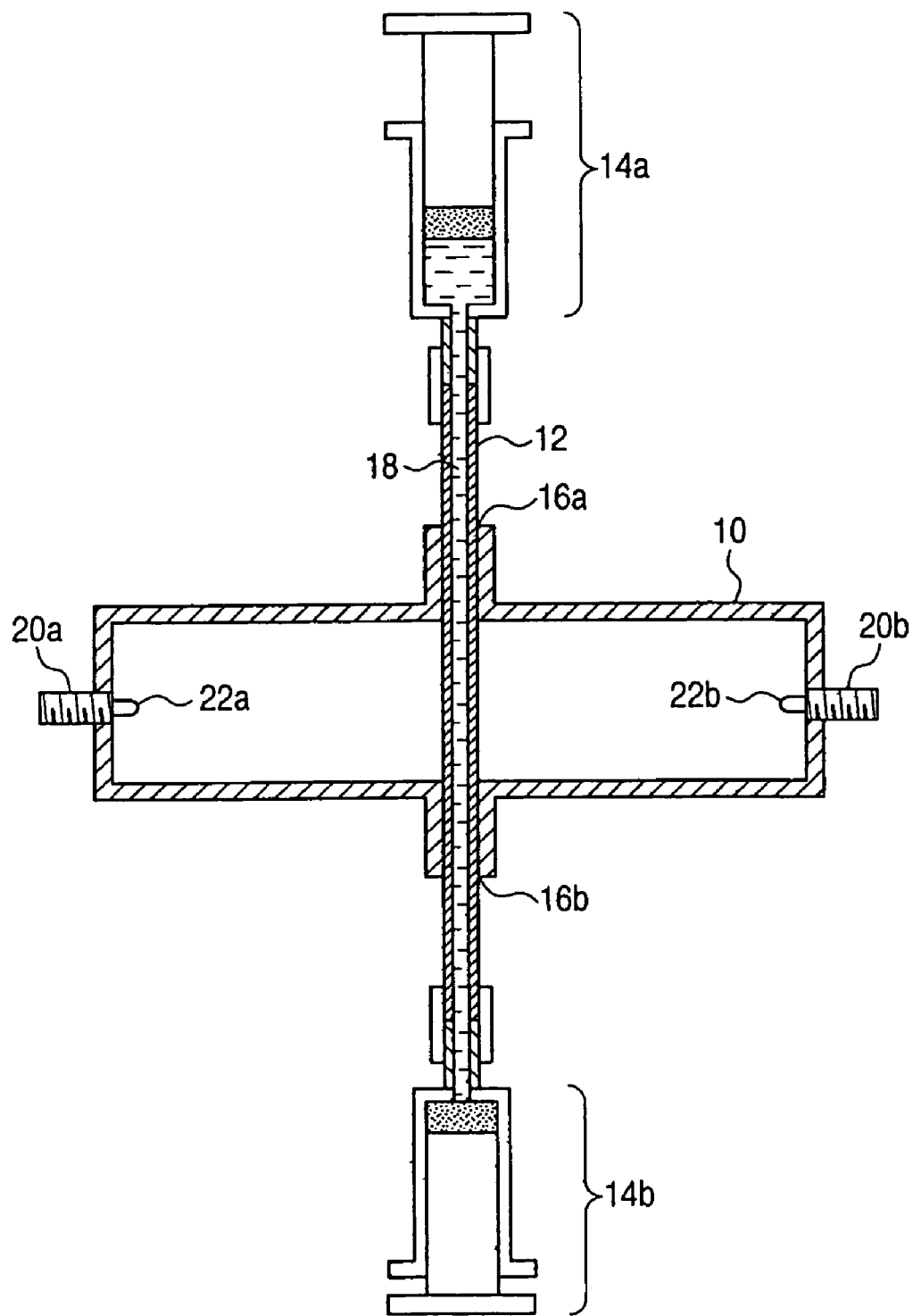
FIG. 3 is a schematic sectional view, taken along an X—X line, of the dielectric substance sealing apparatus 4 shown in FIG. 2.

FIG. 2 is a schematic perspective view of the dielectric substance sealing apparatus 4, and FIG. 3 is a schematic sectional view, taken along an X—X line, of the dielectric substance sealing apparatus 4 shown in FIG. 2.

As shown in FIG. 2, the dielectric substance sealing apparatus 4 includes a cavity resonator 10, a tube 12, a syringe 14a and a syringe 14b.

As shown in FIG. 3, a hole 16a and a hole 16b through which the tube 12 is passed are formed in center portions of upper and lower surfaces of the cavity resonator 10. Also, a connector 20a and a connector 20b both are connected to the network analyzer 6 are formed on a side surface of the cavity resonator 10. A loop antenna 22a and a loop antenna 22b are formed on top end portions of the connector 20a and the connector 20b respectively. The tube 12 is used to seal a mixed substance 18 consisting of the powders and the liquid medium in the cavity resonator 10. In this case, it is preferable that the tube 12 should be formed of the material such as tetrafluoroethylene, or the like with a low dielectric constant and a small loss. The syringe 14a and the syringe 14b are used to inject the mixed substance 18 into the tube 12 and also fluidize the mixed substance 18 in the tube 12.

In the measuring system 2 constructed as above, the relative dielectric constant of the powders is measured as described in the following.

First, a first measuring method out of the method of measuring the relative dielectric constant of powders will be explained hereunder.

In the first measurement of the relative dielectric constant of powders, first either a liquid such as water, alcohol, or the like or a mixed substance in which water, alcohol, and the like are mixed is prepared as the liquid medium. The relative dielectric constant of this liquid medium can be changed if a ratio of the mixed liquid is changed.

The relative dielectric constant of the liquid medium is measured by using the publicly-known liquid-medium relative-dielectric-constant measuring method such as the cavity resonator method, the S-parameter method, the capacitance method, or the like.

Then, the mixed substance 18 in which the powders as the measured object are mixed into the liquid medium is filled into the syringe 14a and the syringe 14b. Then, the syringe 14a is inserted into the tube 12, and then the mixed substance 18 is injected from the syringe 14a into the tube 12.

Then, the syringe 14b is inserted into the tube 12 when the mixed substance 18 is filled in the tube 12.

In this case, it is preferable that, upon blending the powders and the liquid medium, the dispersing agent should be mixed into the liquid medium to accelerate the dispersion of powders into the liquid medium.

The mixed substance 18 injected into the tube 12 is fluidized in the tube 12 by moving pistons of the syringe 14a and the syringe 14b.

The powders are diffused uniformly in the liquid medium by fluidizing the mixed substance 18 in the tube 12. As a result, improvement of a measuring precision of the relative dielectric constant of the powders can be achieved.

Then, the electromagnetic wave fed from the network analyzer 6 is input into the inside of the cavity resonator 10 from the loop antenna 22a. In response to the input of the electromagnetic wave, the electromagnetic wave fed from the cavity resonator 10 is output to the network analyzer 6 via the loop antenna 22b.

In the network analyzer 6, a resonant frequency of the cavity resonator 10 is measured by using the electromagnetic wave that is output from the cavity resonator 10 to the network analyzer 6. As the measured result, the resonant frequency is output from the network analyzer 6 to the processing unit 8.

Then, the relative dielectric constant of the mixed substance 18 is calculated by the processing unit 8.

In this manner, the relative dielectric constant of the mixed substance 18 at a predetermined volume ratio of powders can be calculated by the processing unit 8.

Then, while changing gradually the relative dielectric constant of the liquid medium at the same volume ratio of powders, the relative dielectric constant of the mixed substance 18 with respect to the relative dielectric constant of each liquid medium is calculated by the processing unit 8.

A graph showing a relationship between the relative dielectric constant of the liquid medium and the relative dielectric constant of the mixed substance 18 is made in the processing unit 8.

Figure 4:
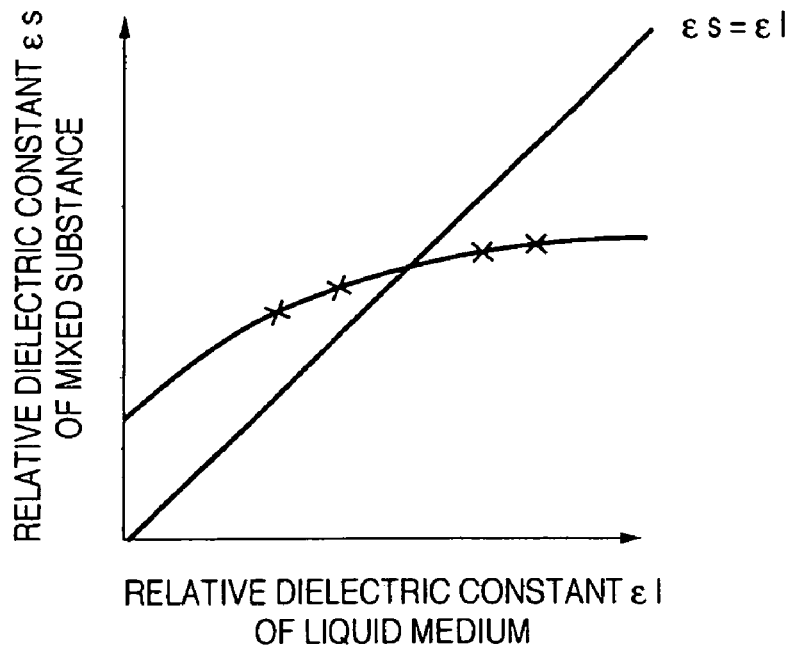
FIG. 4 is a graph showing a relationship between a relative dielectric constant of a liquid medium and a relative dielectric constant of a mixed substance 18.

FIG. 4 is a graph showing the relationship between the relative dielectric constant of the liquid medium and the relative dielectric constant of the mixed substance 18.

Also, in FIG. 4, an abscissa denotes the relative dielectric constant of the liquid medium and an ordinate denotes the relative dielectric constant of the mixed substance 18. Also, an auxiliary line representing respective points at which a value of the relative dielectric constant ($\in$s) of the mixed substance 18 becomes equal to a value of the relative dielectric constant ($\in$1) of the liquid medium, i.e., $\in$s=$\in$1, is depicted.

The relative dielectric constant of the liquid medium is equal to the relative dielectric constant of the mixed substance 18 at an intersection point between a curve indicating the relative dielectric constant of the mixed substance 18 with respect to the relative dielectric constant of the liquid medium and the auxiliary line. The event that the relative dielectric constant of the liquid medium is equal to the relative dielectric constant of the mixed substance 18 is limited to the case that the relative dielectric constant of the liquid medium is equal to the relative dielectric constant of the powders. As a result, in FIG. 4, the relative dielectric constant of the liquid medium and the relative dielectric constant of the mixed substance 18, both having the same value, at the intersection point between the curve and the auxiliary line yield the relative dielectric constant of the powders.

In FIG. 4, the relative dielectric constant of the powders is derived from the intersection point between the curve indicating the relative dielectric constant of the mixed substance 18 with respect to the relative dielectric constants of the liquid media that are estimated respectively based on the detected relative dielectric constant of the mixed substance 18, i.e., the relative dielectric constant of the mixed substance 18 that is derived by interpolating a plurality of measuring points of the mixed substance 18, and the auxiliary line.

Figure 5:
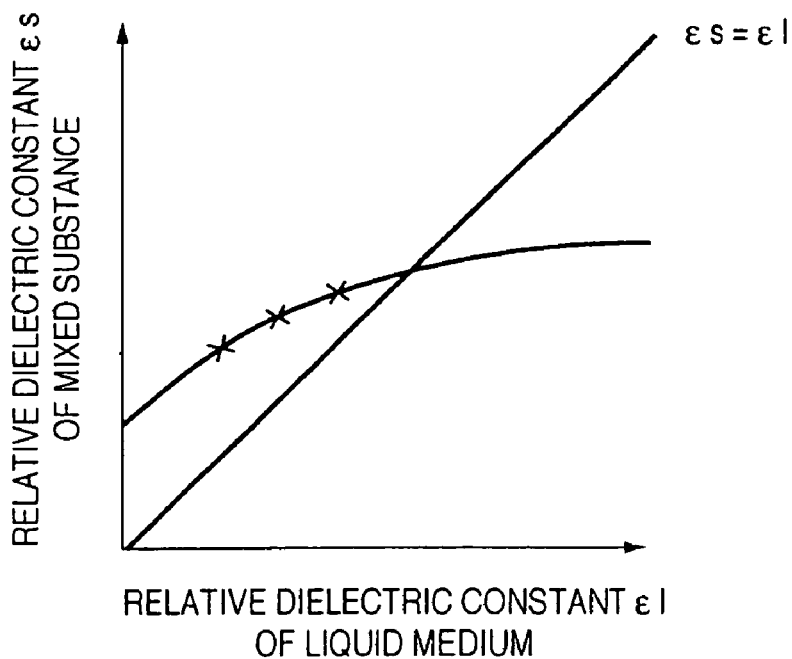
FIG. 5 is a graph showing another relationship between the relative dielectric constant of the liquid medium and the relative dielectric constant of the mixed substance 18.

FIG. 5 is a graph showing another relationship between the relative dielectric constant of the liquid medium and the relative dielectric constant of the mixed substance 18. Also, in FIG. 5, an abscissa denotes the relative dielectric constant of the liquid medium and an ordinate denotes the relative dielectric constant of the mixed substance 18. Also, an auxiliary line representing respective points at which a value of the relative dielectric constant ($\in$s) of the mixed substance 18 becomes equal to a value of the relative dielectric constant ($\in$1) of the liquid medium, i.e., $\in$s=$\in$1, is depicted.

Unlike FIG. 4, FIG. 5 shows the method of deriving the relative dielectric constant of the powders when the relative dielectric constant of the powders cannot be detected from the intersection point between the curve indicating the detected relative dielectric constant of the mixed substance 18 and the relative dielectric constant of the mixed substance 18 obtained by the interpolation, i.e., the relative dielectric constant of the mixed substance 18 within the interpolation range, and the auxiliary line.

More concretely, as shown in FIG. 5, the relative dielectric constant of the mixed substance 18 out of the interpolation range is estimated based on the relative dielectric constant of the mixed substance 18 within the interpolation range. In other words, the relative dielectric constant of the powders is detected from the intersection point between the curve of the relative dielectric constant of the mixed substance 18, which is derived by executing the extrapolation based on a plurality of measuring points of the mixed substance 18, and the auxiliary line.

As explained above, according to the present embodiment, the relative dielectric constant of the powders can be detected by detecting the point at which the relative dielectric constant of the mixed substance 18 becomes equal to the relative dielectric constant of the liquid medium. As a result, the relative dielectric constant of powders can be detected with high precision.

Next, a second measuring method out of the method of measuring the relative dielectric constant of powders will be explained hereunder.

In this measurement of the relative dielectric constant of powders, first a liquid medium such as an ion-exchange water, or the like is prepared.

Then, the mixed substance 18 in which the powders as the measured object are mixed into the liquid medium is filled in the syringe 14a and the syringe 14b.

Then, the syringe 14a is inserted into the tube 12, and then the mixed substance 18 is injected from the syringe 14a into the tube 12.

Then, the syringe 14b is inserted into the tube 12 when the mixed substance 18 is filled in the tube 12.

In this case, it is preferable that, upon blending the powders and the liquid medium, the dispersing agent should be mixed into the liquid medium to accelerate the dispersion of the powders into the liquid medium.

The mixed substance 18 injected into the tube 12 is fluidized in the tube 12 by moving the pistons of the syringe 14a and the syringe 14b.

The powders are diffused uniformly in the liquid medium by fluidizing the mixed substance 18 in the tube 12. As a result, improvement of a measuring precision of the relative dielectric constant of the powders can be achieved.

Then, the electromagnetic wave fed from the network analyzer 6 is input into the inside of the cavity resonator 10 from the loop antenna 22a. In response to the input of the electromagnetic wave, the electromagnetic wave fed from the cavity resonator 10 is output to the network analyzer 6 via the loop antenna 22b.

In the network analyzer 6, the resonant frequency of the cavity resonator 10 in a $TM_{010}$ mode is measured by using the electromagnetic wave that is output from the cavity resonator 10 to the network analyzer 6. As the measured result, the resonant frequency is output from the network analyzer 6 to the processing unit 8. Then, the relative dielectric constant of the mixed substance 18 is calculated by the processing unit 8.

In this way, the relative dielectric constant of the mixed substance 18 at a predetermined volume ratio of powders can be calculated by the processing unit 8.

In this case, processing procedures executed up to now are similar to those in the above first measuring method.

Then, in order to improve a measuring precision of the relative dielectric constants of the powders, the relative dielectric constant of the mixed substance 18 is derived by the processing unit 8 while changing gradually the volume ratio of the powders occupied in the mixed substance 18 that is injected into the tube 12.

Then, the processing unit 8 applies the formula such as the logarithmic mixture rule, the Lichtenecker-Rother's Formula, or the like, which is used to calculate the relative dielectric constants of powders from the relative dielectric constant of the mixed substance 18, to the relative dielectric constant of the mixed substance 18 calculated in this manner to calculate the relative dielectric constants of powders.

A graph showing a relationship between the volume ratio of the powders and the relative dielectric constant of the mixed substance 18 is made in the processing unit 8.

Figure 6:
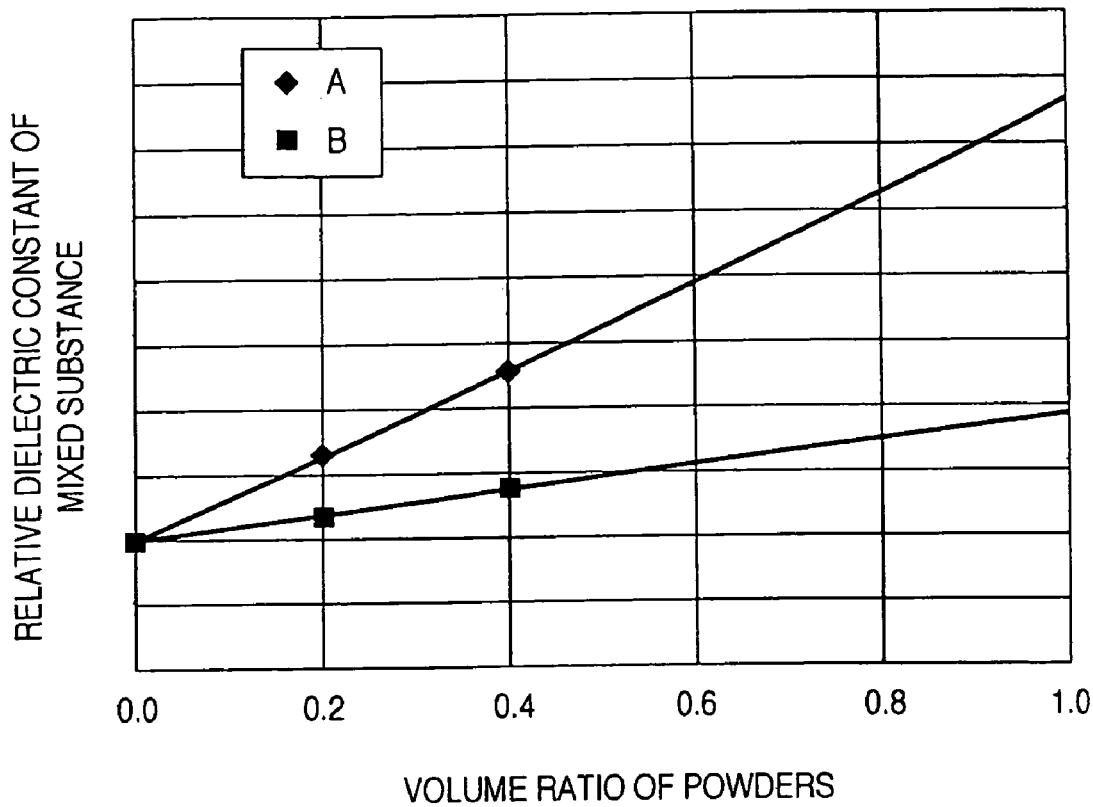
FIG. 6 is a graph showing a relationship between a volume ratio of powders and the relative dielectric constant of the mixed substance 18.

FIG. 6 is a graph obtained by fitting the logarithmic mixture rule to a relationship between the volume ratio of the powders and the relative dielectric constant of the mixed substance 18 based on the method of least squares. In FIG. 6, an abscissa denotes the volume ratio of powders and an ordinate denotes the relative dielectric constant of the mixed substance 18.

In FIG. 6, the fact that the volume ratio of the powders is 1.0 signifies that the liquid medium is not present in the mixed substance 18 and merely the powders are present.

Therefore, a value of the relative dielectric constant obtained when the volume ratio of the powders is 1.0 corresponds to the relative dielectric constant of the powders. Thus, the relative dielectric constant of the powders is detected by reading the value of the relative dielectric constant obtained when the volume ratio of the powders is 1.0 from the curve shown in FIG. 6.

The curve shown in FIG. 6 is plotted by detecting the relative dielectric constant of the mixed substance 18 with respect to the volume ratio of the powders by estimating the relative dielectric constant of the mixed substance 18 out of the measuring range based on the detected relative dielectric constant of the mixed substance 18, i.e., by detecting the relative dielectric constant of the mixed substance 18 by extrapolating a plurality of measuring points of the mixed substance 18.

In FIG. 6, the fact that the volume ratio of the powders is 0.0 signifies that no powder is present in the mixed substance 18 and merely the liquid medium is present.

Therefore, a value of the relative dielectric constant obtained when the volume ratio of powders is 0.0 gives the relative dielectric constant of the liquid medium.

For this reason, in case the relative dielectric constant of the liquid medium is extremely lower or higher than the relative dielectric constant of the powders, a change of a gradient of the curve become steep. Thus, it is possible that a measuring precision of the relative dielectric constant of the powders derived by the extrapolation is worsened.

Therefore, if the liquid medium having a value of the relative dielectric constant close to a value of the detected relative dielectric constant of powders is selected, it is possible to prevent the deterioration of the measuring precision when the relative dielectric constant of powders is derived by the extrapolation.

As the criterion applied to select the liquid medium having a value of the relative dielectric constant close to the value of the detected relative dielectric constant of powders, a value of the relative dielectric constant of the ceramic composition made of the measured powders is employed.

If the liquid medium having the relative dielectric constant that is 0.5 times to 2.0 times the relative dielectric constant of the ceramic composition made of the powders is selected, a measuring precision of the relative dielectric constant of the powders can be improved.

In this case, the foregoing logarithmic mixture rule or Lichtenecker-Rother's Formula is given in the following. As well known, the logarithmic mixture rule is given by the following formula.

$$\log \in_r = v1 \log \in_{r1} + v2 \log \in_{r2}$$

Also, the Lichtenecker-Rother's Formula is given by the following formula.

$$\in_r^k = v1 \in_{r1}^k + v2 \in_{r2}^k$$

Where

∈$_r$: relative dielectric constant of powders
∈$_{r1}$: relative dielectric constant of the liquid medium
∈r2: relative dielectric constant of the mixed substance 18
v1: volume ratio of the liquid medium
v2: volume ratio of powders
k: fitting parameter ($-1 \leq k \leq 1$).

As explained above, according to the second measuring method, the relative dielectric constant of powders can be detected by using the liquid medium a value of the relative dielectric constant of which is close to a value of the detected relative dielectric constant of powders. As a result, the relative dielectric constant of powders can be derived with high precision.

In the first and second measuring methods, the mixed substance 18 injected into the tube 12 is fluidized by using the syringe 14a and the syringe 14b. In this case, the mixed substance 18 may be fluidized by using a fluidizing apparatus 38A shown in FIG. 7.

Figure 7:
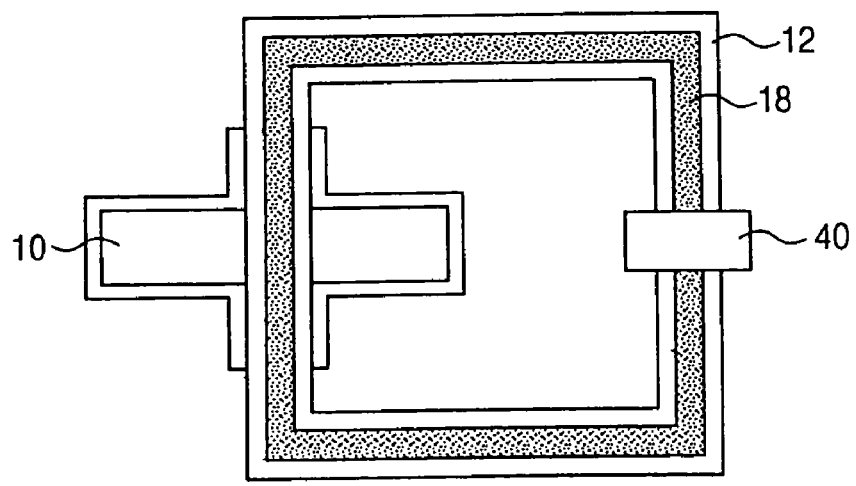
FIG. 7 is a schematic view showing a fluidizing apparatus 38A using a pump.

FIG. 7 is a schematic view showing a fluidizing apparatus 38A using a pump.

The fluidizing apparatus 38A shown in FIG. 7 fluidizes the mixed substance 18 by circulating this mixed substance 18 by using a pump 40.

The powders in the mixed substance 18 can be diffused uniformly by using the fluidizing apparatus 38A shown in FIG. 7. As a result, improvement of the measuring precision of the relative dielectric constant of the powders can be attained.

Next, another preferred embodiment of the present invention will be explained hereunder.

Figure 8:
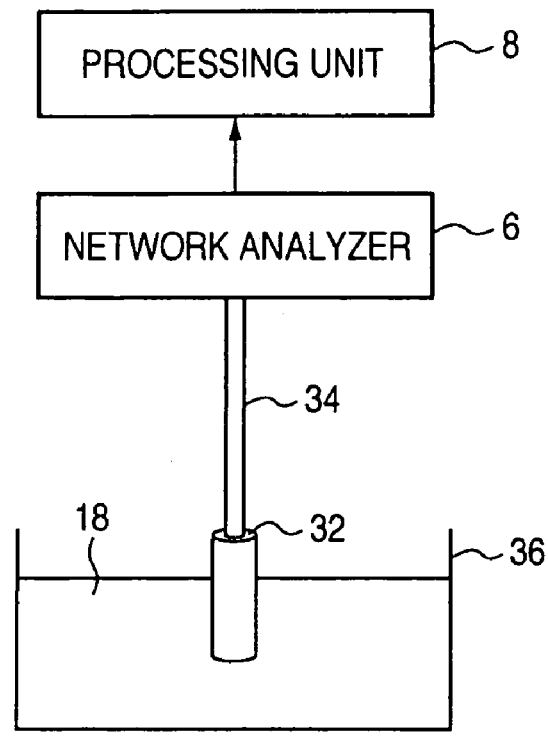
FIG. 8 is a sectional view of a measuring system for executing a method of measuring the relative dielectric constant of powders according another preferred embodiment of the present invention.

FIG. 8 is a sectional view of a measuring system for implementing the method of measuring the relative dielectric constant of powders according another preferred embodiment of the present invention.

As shown in FIG. 8, a measuring system 30 includes the network analyzer 6, the processing unit 8, a probe 32, a cable 34, and a vessel 36.

The network analyzer 6 and the processing unit 8 are same as those constituting the measuring system 2.

The probe 32 is a coaxial cable that inputs the electromagnetic wave fed from the network analyzer 6 into the mixed substance 18 contained in the vessel 36. This probe 32 is connected to the network analyzer 6 via the cable 34.

In the measuring system 30 constructed as above, the relative dielectric constant of the powders is measured as described in the following.

First, like the case that the relative dielectric constant of powders is measured by the measuring system 2, the liquid such as water, alcohol, or the like or the mixed substance in which water, alcohol, and the like are mixed is prepared as the liquid medium. The relative dielectric constant of the liquid medium is measured by using the publicly-known liquid-medium relative-dielectric-constant measuring method such as the cavity resonator method, the S-parameter method, the capacitance method, or the like.

Then, the mixed substance 18 in which the powders as the measured object are mixed in the liquid medium is contained into the vessel 36. Then, the electromagnetic wave fed from the network analyzer 6 is input into the mixed substance 18 from the probe 32 via the cable 34.

In response to the input of the electromagnetic wave, such electromagnetic wave is output to the network analyzer 6 from the probe 32 via the cable 34.

In the network analyzer 6, a reflection coefficient between an end surface of the probe 32 and the mixed substance 18 is measured based on the electromagnetic wave that is output from the probe 32 to the network analyzer 6. The reflection coefficient is output to the processing unit 8 from the network analyzer 6 as the measured result. The relative dielectric constant of the mixed substance 18 is calculated in the processing unit 8.

By now, it is preferable that an ultrasonic wave should be input into the vessel 36 from an ultrasonic generator (not shown) to fluidize the mixed substance 18.

When the relative dielectric constant of the mixed substance 18 is calculated in the processing unit 8, a graph showing a relationship between the relative dielectric constant of the liquid medium and the relative dielectric constant of the mixed substance 18 is made in the same manner as in the above measuring system 2, and also the relative dielectric constant of the powders is calculated.

As explained above, according to another preferred embodiment of the present invention, the relative dielectric constant of powders can be derived by using the probe 32. Therefore, the relative dielectric constant of powders can be detected with high precision.

Figure 9:
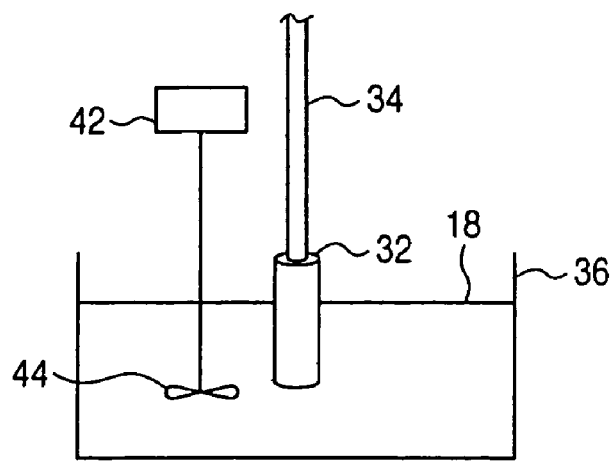
FIG. 9 is a schematic view showing a fluidizing apparatus 38B using stirring blades.

Also, in the above embodiment, the mixed substance 18 contained in the vessel 36 is circulated by using the ultrasonic wave, but such mixed substance 18 may be circulated by using a circulating apparatus 38B shown in FIG. 9. FIG. 9 is a schematic view showing the circulating apparatus 38B using stirring blades.

As shown in FIG. 9, the fluidizing apparatus 38B fluidizes the mixed substance 18 by causing stirring blades 44 connected to a motor 42 to rotate.

The powders in the mixed substance 18 can be diffused uniformly by using the fluidizing apparatus 38B shown in FIG. 9. As a result, improvement of a measuring precision of the relative dielectric constant of powders can be attained.

In order to clarify much more advantages of the present invention, various Examples will be given hereinafter.

At first, Example according to the first measuring method will be explained hereunder.

EXAMPLE 1

$Al_2O_3$ powders were prepared as the sample of the powder dielectric substance, and a mixed substance in which the ion-exchange water and the alcohol are mixed was prepared as the liquid medium. Also, the measuring system 2 shown in FIG. 1 was employed as the measuring system.

Then, the mixed substance 18 in which the sample as the measured object is mixed in the liquid substance was prepared, and then filled in the syringe 14a and the syringe 14b. The volume ratio of the powders in the sample was set to 0.1 in the mixed substance 18. The relative dielectric constant of the liquid medium was measured by using the cavity resonator method.

Then, the syringe 14a was inserted into the tube 12 and then the mixed substance 18 was injected into the tube 12. Then, the syringe 14b was inserted into the tube 12 when the mixed substance 18 was filled in the tube 12.

The mixed substance 18 injected into the tube 12 was fluidized in the tube 12 by moving the pistons of the syringe 14a and the syringe 14b.

Here, a cavity resonator having a diameter of 80 mm and a height of 10 mm was used as the cavity resonator 10, and a tube made of tetrafluoroethylene to have an inner diameter of 1 mm and an outer diameter of 3 mm was used as the tube 12.

Then, the electromagnetic wave of 2.5 to 3.0 GHz fed from the network analyzer 6 was input into the cavity resonator 10 from the loop antenna 22a.

In response to the input of the electromagnetic wave, such electromagnetic wave fed from the cavity resonator 10 was output to the network analyzer 6 via the loop antenna 22b. The resonant frequency of the cavity resonator 10 in a $TM_{010}$ mode was measured by the network analyzer 6 based on the electromagnetic wave that was output from the cavity resonator 10 to the network analyzer 6. The resonant frequency was 2.86 GHz. The resonant frequency was output from the network analyzer 6 to the processing unit 8 as the measured result, and then the relative dielectric constant of the mixed substance 18 was calculated by the processing unit 8.

In this way, the relative dielectric constant of the mixed substance 18 in which the volume ratio of the sample is 0.1 was calculated by the processing unit 8.

Then, while changing gradually the relative dielectric constant of the liquid medium in a range from 8 to 14.7 at the same volume ratio, the relative dielectric constant of the mixed substance 18 with respect to the relative dielectric constant of each liquid medium was calculated by the processing unit 8.

A graph showing a relationship between the relative dielectric constant of the liquid medium and the relative dielectric constant of the mixed substance 18 was made in the processing unit 8.

Figure 10:
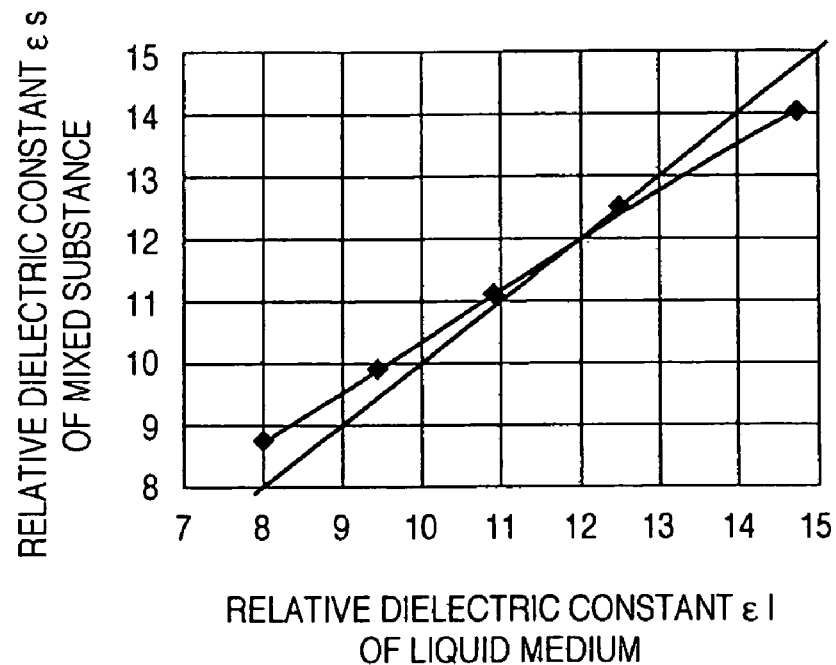
FIG. 10 is a graph showing a relationship between the relative dielectric constant of the liquid medium and the relative dielectric constant of the mixed substance 18 in Example 1.

FIG. 10 is a graph showing the relationship between the relative dielectric constant of the liquid medium and the relative dielectric constant of the mixed substance 18. Also, in FIG. 10, an abscissa denotes the relative dielectric constant of the liquid medium and an ordinate denotes the relative dielectric constant of the mixed substance 18. Also, an auxiliary line representing respective points at which a value of the relative dielectric constant (∈s) of the mixed substance 18 becomes equal to a value of the relative dielectric constant (∈1) of the liquid medium, i.e., ∈s=∈1, is depicted.

Both the relative dielectric constant of the liquid medium and the relative dielectric constant of the mixed substance 18 were given as 12.07 at the intersection point between the curve showing the relative dielectric constant of the mixed substance 18 with respect to the relative dielectric constant of each liquid medium and the auxiliary line. As a result, the relative dielectric constant of the detected $Al_2O_3$ powders was calculated as 12.07.

EXAMPLE 2

Four types of powders consisting of sample A, sample B, sample C, and sample D respectively were prepared as the samples.

All these powders were made of $Ba(NdBi)_2TiO_4$. The sample A was formed by breaking tentatively sintered powders, the sample B was formed of spherical powders, the sample C was formed of spherical powders, and the sample D was formed by breaking the sample C.

As the liquid medium of the sample, the mixed substance in which the ion-exchange water, the alcohol, and the 0.3 wt % dispersing agent are mixed was prepared.

In this case, a volume ratio of the sample A in the mixed substance 18 was set to 0.2, a volume ratio of the sample B was set to 0.2, a volume ratio of the sample C was set to 0.4, and a volume ratio of the sample D was set to 0.4.

The mixed substances 18 in which the sample A, the sample B, the sample C, and the sample D as the measured object are mixed in the liquid medium respectively were prepared. Then, the relative dielectric constants of respective mixed substances 18 were calculated by using the measuring system 2 shown in FIG. 1 as the measuring system.

In Example 2, the relative dielectric constants of the mixed substances 18 containing the sample A, the sample B, the sample C, and the sample D respectively were calculated while changing the relative dielectric constant of the liquid medium in a range from 66 to 77.

Figure 11:
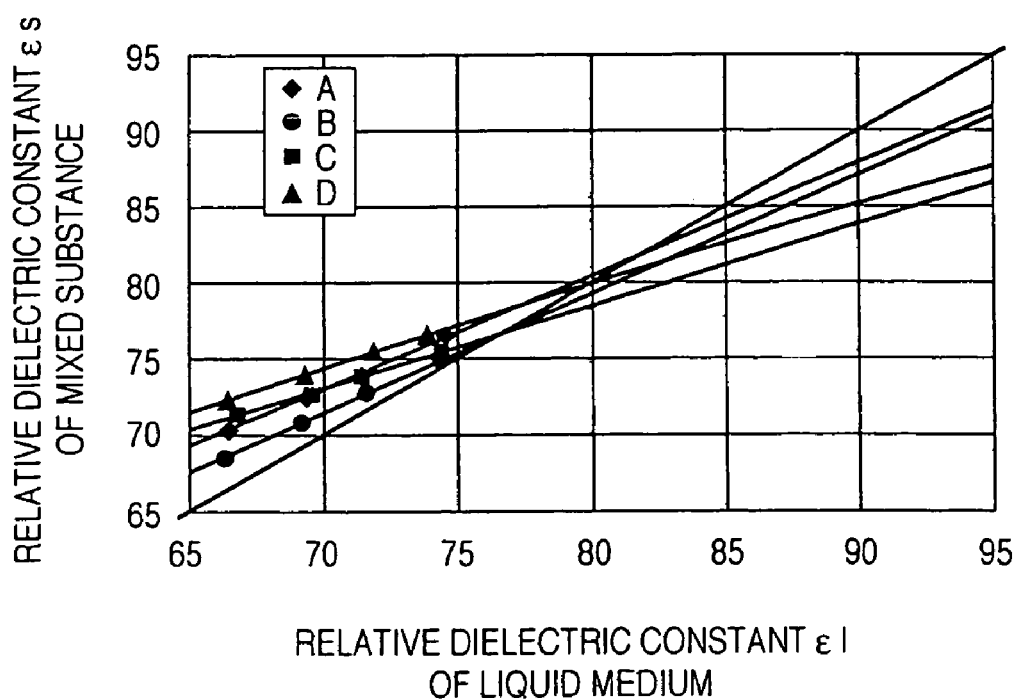
FIG. 11 is a graph showing a relationship between the relative dielectric constant of the liquid medium and the relative dielectric constant of the mixed substance 18 in Example 2.

FIG. 11 is a graph showing a relationship between the relative dielectric constant of the liquid medium and the relative dielectric constant of the mixed substance 18. Also, in FIG. 11, an abscissa denotes the relative dielectric constant of the liquid medium and an ordinate denotes the relative dielectric constant of the mixed substance 18. Also, an auxiliary line representing respective points at which a value of the relative dielectric constant (∈s) of the mixed substance 18 becomes equal to a value of the relative dielectric constant (∈1) of the liquid medium, i.e., ∈s=∈1, is depicted.

The relative dielectric constants of the sample A, the sample B, the sample C, and the sample D were calculated by reading the relative dielectric constant of the liquid medium and the relative dielectric constant of the mixed substance 18 at the intersection point between the curve and the auxiliary line, in the same way as in Example 1.

The relative dielectric constant of the sample A was calculated as 82.22, the relative dielectric constant of the sample B was calculated as 77.71, the relative dielectric constant of the sample C was calculated as 77.34, and the relative dielectric constant of the sample D was calculated as 79.78.

EXAMPLE 3

In Example 3, the same samples as in Example 2, i.e., four types of powder dielectric substances consisting of the sample A, the sample B, the sample C, and the sample D respectively were prepared as the samples.

As the liquid medium in the sample, the mixed substance in which $BaTiO_3$ powders and the dispersing agent are mixed in the ion-exchange water was prepared.

In this case, a volume ratio of the sample A in the mixed substance 18 was set to 0.2, a volume ratio of the sample B was set to 0.2, a volume ratio of the sample C was set to 0.4, and a volume ratio of the sample D was set to 0.4.

The mixed substances 18 in which the sample A, the sample B, the sample C, and the sample D as the measured object are mixed in the liquid medium respectively were prepared, like Example 2. Then, the relative dielectric constants of respective mixed substances 18 were calculated by using the measuring system 2 shown in FIG. 1 as the measuring system.

In Example 3, the relative dielectric constants of the mixed substances 18 containing the sample A, the sample B, the sample C, and the sample D respectively were calculated while changing the relative dielectric constant of the liquid medium in a range from 74 to 96.

Figure 12:
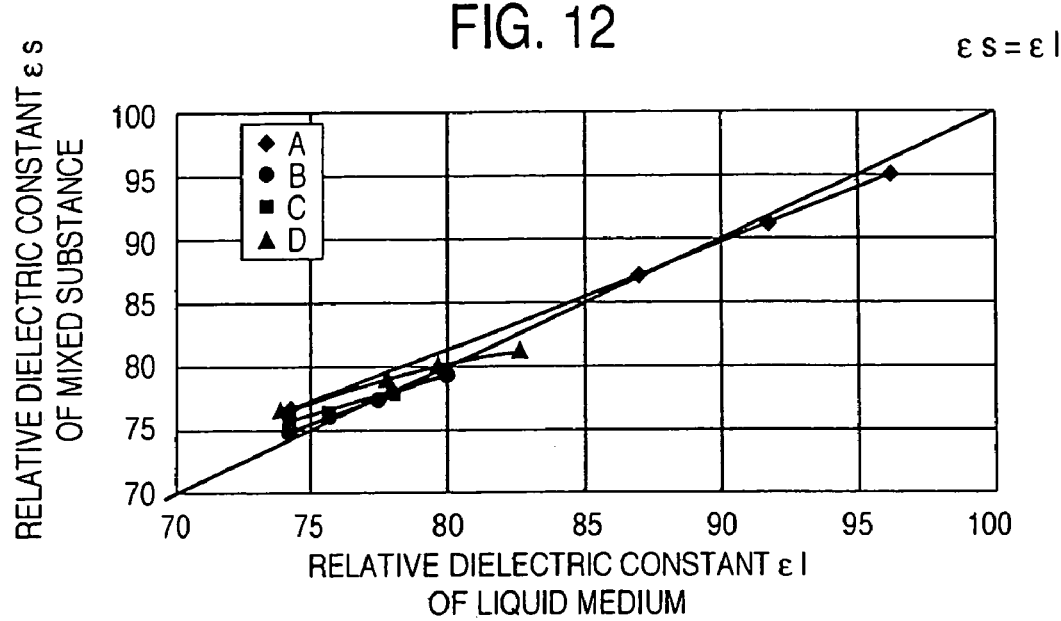
FIG. 12 is a graph showing a relationship between the relative dielectric constant of the liquid medium and the relative dielectric constant of the mixed substance 18 in Example 3.

FIG. 12 is a graph showing a relationship between the relative dielectric constant of the liquid medium and the relative dielectric constant of the mixed substance 18. Also, in FIG. 12, an abscissa denotes the relative dielectric constant of the liquid medium and an ordinate denotes the relative dielectric constant of the mixed substance 18.

The relative dielectric constants of the sample A, the sample B, the sample C, and the sample D were calculated by reading the relative dielectric constant of the liquid medium and the relative dielectric constant of the mixed substance 18 at the intersection point between the curve and the auxiliary line, in the same way as in Example 1.

The relative dielectric constant of the sample A was calculated as 88.71, the relative dielectric constant of the sample B was calculated as 77.80, the relative dielectric constant of the sample C was calculated as 78.04, and the relative dielectric constant of the sample D was calculated as 80.32.

In Example 2 and Example 3, calculated results of the relative dielectric constants of the sample A, the sample B, the sample C, and the sample D are given in Table 1.

TABLE 1

|  | sample A | sample B | sample C | sample D |
| --- | --- | --- | --- | --- |
| Example 2 | 82.22 | 77.71 | 77.34 | 79.78 |
| Example 3 | 88.71 | 77.80 | 78.04 | 80.32 |

As given in Table 1, the relative dielectric constants of respective samples became substantially equal when such relative dielectric constants were measured after the relative dielectric constant of the liquid medium was changed respectively.

Next, Examples according to the second measuring method will be explained hereunder.

EXAMPLE 4

Three types of powders consisting of sample A, sample B, and sample C respectively were prepared as the samples.

All these powders were made of Ba(NdBi)$_2$TiO$_4$. The sample A was formed by breaking the tentatively sintered powders, the sample B was formed of the spherical powders, and the sample C was formed by breaking the sample B.

As the liquid medium of the sample, the mixed substance consisting of the 99.7 wt % ion-exchange water and the 0.3 wt % dispersing agent was prepared. The measuring system 2 shown in FIG. 1 was employed as the measuring system.

Here, the relative dielectric constant of the ceramic composition in the sample was 93 and the relative dielectric constant of the liquid medium was 74. Thus, the relative dielectric constant of the liquid medium was 0.80 times the relative dielectric constant of the ceramic composition powders.

Then, the mixed substance 18 in which the sample A as the measured object is mixed in the liquid medium was prepared and then filled in the syringe 14*a* and the syringe 14*b*. The mixed substance 18 was prepared in such a manner that the volume ratio of the powders in the sample A became 0.4.

Then, the syringe 14*a* was inserted into the tube 12 and then the mixed substance 18 was injected into the tube 12. Then, the syringe 14*b* was inserted into the tube 12 when the mixed substance 18 was filled in the tube 12.

The mixed substance 18 injected into the tube 12 was fluidized in the tube 12 by moving the pistons of the syringe 14*a* and the syringe 14*b*.

Here, the cavity resonator having a diameter of 80 mm and a height of 10 mm was used as the cavity resonator 10, and the tube formed of tetrafluoroethylene to have an inner diameter of 1 mm and an outer diameter of 3 mm was used as the tube 12.

Then, the electromagnetic wave of 2.5 to 3.0 GHz fed from the network analyzer 6 was input into the cavity resonator 10 from the loop antenna 22*a*.

In response to the input of the electromagnetic wave, such electromagnetic wave fed from the cavity resonator 10 was output to the network analyzer 6 via the loop antenna 22*b*.

The resonant frequency of the cavity resonator 10 in a TM$_{010}$ mode was measured by the network analyzer 6 based on the electromagnetic wave that was output from the cavity resonator 10 to the network analyzer 6. The resonant frequency was 2.86 GHz. The resonant frequency was output from the network analyzer 6 to the processing unit 8 as the measured result, and then the relative dielectric constant of the mixed substance 18 was calculated by the processing unit 8.

In this fashion, the relative dielectric constant of the mixed substance 18 in which the volume ratio of the sample A was 0.4 was calculated by the processing unit 8.

Then, while changing gradually the volume ratio of the sample A occupied in the mixed substance 18 in a range from 0 to 0.4, the relative dielectric constant of the mixed substance 18 was calculated in the same way as the case that the volume ratio of the sample A was 0.4.

A graph showing a relationship between the volume ratio of the powders and the relative dielectric constant of the mixed substance 18 was made in the processing unit 8.

Figure 13:
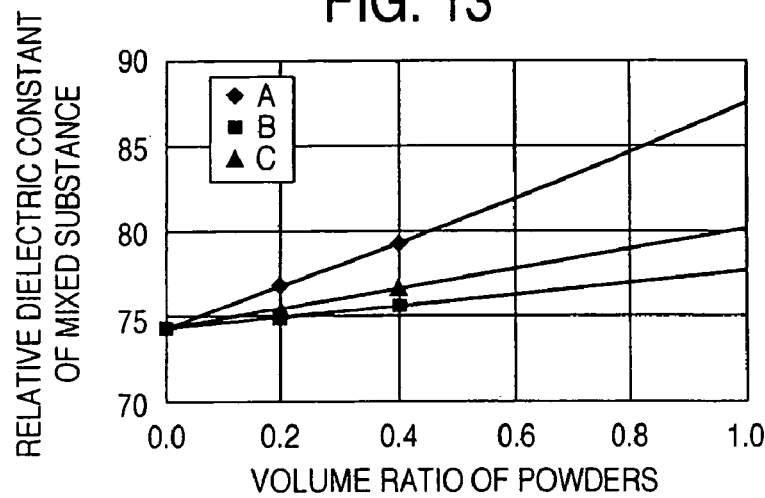
FIG. 13 is a graph showing a relationship between the volume ratio of powders and the relative dielectric constant of the mixed substance 18 in Example 4.

FIG. 13 is a graph obtained by fitting the logarithmic mixture rule to the relationship between the volume ratio of the powders and the relative dielectric constant of the mixed substance 18 based on the method of least squares.

Also, in FIG. 13, an abscissa denotes the volume ratio of the powders and an ordinate denotes the relative dielectric constant of the mixed substance 18.

Figure 14:
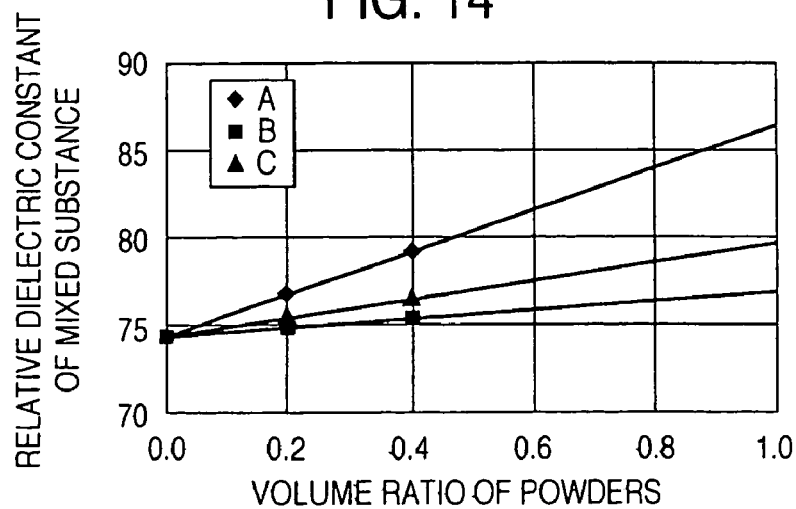
FIG. 14 is a graph showing another relationship between the volume ratio of powders and the relative dielectric constant of the mixed substance 18 in Example 4.

FIG. 14 is a graph obtained by fitting the Lichtenecker-Rother's Formula to the relationship between the volume ratio of the powders and the relative dielectric constant of the mixed substance 18 based on the method of least squares.

Also, in FIG. 14, an abscissa denotes the volume ratio of the powders and an ordinate denotes the relative dielectric constant of the mixed substance 18.

In FIG. 13, the relative dielectric constant of the sample A was detected by reading a value of the relative dielectric constant when the volume ratio of the powders is 1.0.

Also, in FIG. 14, the relative dielectric constant of the sample A was detected by reading a value of the relative dielectric constant when the volume ratio of the powders is 1.0.

Then, the relative dielectric constants of the sample B and the sample C were detected in the same way as in the case that the relative dielectric constant of the sample A was measured.

Measured results of the relative dielectric constants of the samples A, B, C are given in Table 2.

TABLE 2

|  | logarithmic mixture rule | Lichtenecker-Rother's Formula |
| --- | --- | --- |
| sample A | 87.5 | 86.3 |
| sample B | 77.7 | 76.8 |
| sample C | 80.2 | 79.6 |

As given in Table 2, the relative dielectric constants of the samples A, B, C derived by using the logarithmic mixture rule and the Lichtenecker-Rother's Formula became almost equal mutually.

EXAMPLE 5

As the sample, the spherical powders made of Ba (NdBi)$_2$ TiO$_4$ were prepared.

As the liquid medium, the mixed substance in which the 15.65 wt % BaTiO$_3$ powders and the 0.3 wt % dispersing agent are mixed in the 84.10 wt % ion-exchange water was prepared.

Like Example 4, the mixed substance 18 in which the sample as the measured object is mixed in the liquid medium, in which the ion-exchange water, the BaTiO$_3$ powders and the dispersing agent are mixed, was prepared. The relative dielectric constant of the mixed substance 18 was calculated by using the measuring system 2 shown in FIG. 1 as the measuring system.

Here, the relative dielectric constant of the ceramic composition in the sample was 93 and the relative dielectric constant of the liquid medium was 80.1. Thus, the relative dielectric constant of the liquid medium was 0.86 times the relative dielectric constant of the ceramic composition powders.

In Example 5, the relative dielectric constant of the mixed substance 18 was detected while changing gradually the volume ratio of the sample occupied in the mixed substance 18 in a range from 0 to 0.4.

A graph showing a relationship between the volume ratio of the powders and the relative dielectric constant of the mixed substance 18 was made in the processing unit 8.

Figure 15:
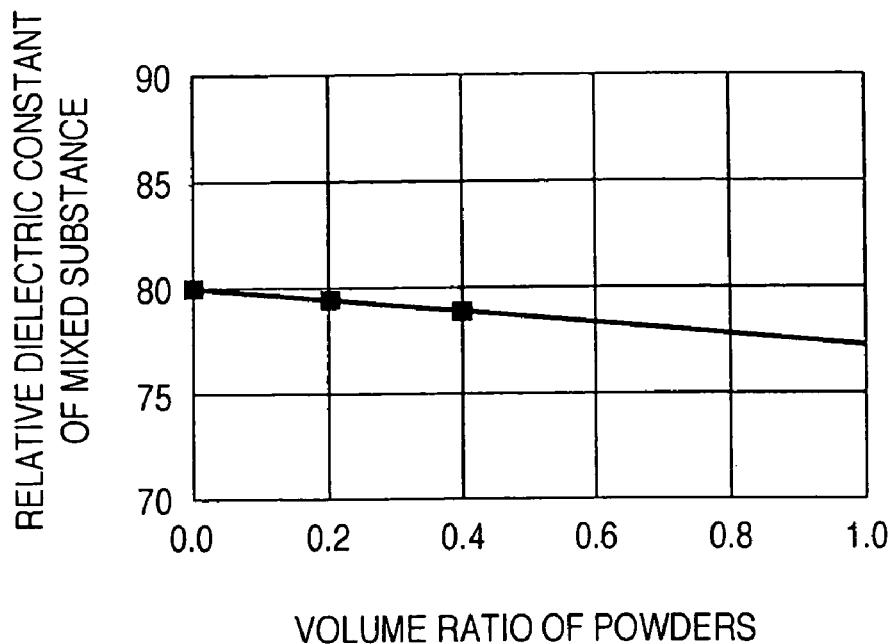
FIG. 15 is a graph showing a relationship between the volume ratio of powders and the relative dielectric constant of the mixed substance 18 in Example 5.

FIG. 15 is a graph obtained by fitting the logarithmic mixture rule to the relationship between the volume ratio of the powders and the relative dielectric constant of the mixed substance 18 based on the method of least squares.

In FIG. 15, an abscissa denotes the volume ratio of the powders and an ordinate denotes the relative dielectric constant of the mixed substance 18.

FIG. 16 is a graph obtained by fitting the Lichtenecker-Rother's Formula to the relationship between the volume ratio of the powders and the relative dielectric constant of the mixed substance 18 based on the method of least squares.

In FIG. 16, an abscissa denotes the volume ratio of the powders and an ordinate denotes the relative dielectric constant of the mixed substance 18.

Like Example 5, in FIG. 15, the relative dielectric constant of the sample was detected by reading a value of the relative dielectric constant when the volume ratio of the powders is 1.0.

Also, in FIG. 16, the relative dielectric constant of the sample was detected by reading a value of the relative dielectric constant when the volume ratio of the powders is 1.0.

The relative dielectric constant of the sample detected by using the logarithmic mixture rule was 77.7, while the relative dielectric constant of the sample detected by using the Lichtenecker-Rother's Formula was 77.3. Thus, both relative dielectric constants became almost equal values mutually.

EXAMPLE 6

As the sample, the $Al_2O_3$ powders were prepared. As the liquid medium, the mixed substance in which the ion-exchange water and methanol are mixed was prepared.

Five types of liquid media consisting of the liquid medium A (relative dielectric constant 10.23), the liquid medium B (same 14.08), the liquid medium C (same 18.26), the liquid medium D (same 22.88), and the liquid medium E (same 41.69) were prepared while changing an amount of methanol that is mixed into the ion-exchange water.

The relative dielectric constant of the mixed substance 18 was calculated by employing the measuring system 2 shown in FIG. 1 as the measuring system. Now, the relative dielectric constant of the ceramic composition of the sample was 11. Thus, the relative dielectric constants of five type liquid media were 0.93 times (liquid medium A), 1.28 times (liquid medium B), 1.66 times (liquid medium C), 2.08 times (liquid medium D), and 3.79 times (liquid medium E) the ceramic composition of the sample respectively.

In Example 6, the relative dielectric constant of the mixed substance 18 was detected while changing gradually the volume ratio of the sample occupied in the mixed substance 18 to the liquid medium A in a range from 0 to 0.2.

A graph showing a relationship between the volume ratio of the powders and the relative dielectric constant of the mixed substance 18 was made in the processing unit 8.

FIG. 17 is a graph obtained by fitting the logarithmic mixture rule to the relationship between the volume ratio of the powders and the relative dielectric constant of the mixed substance 18 based on the method of least squares.

In FIG. 17, an abscissa denotes the volume ratio of the powders and an ordinate denotes the relative dielectric constant of the mixed substance 18.

FIG. 18 is a graph obtained by fitting the Lichtenecker-Rother's Formula to the relationship between the volume ratio of the powders and the relative dielectric constant of the mixed substance 18 based on the method of least squares.

In FIG. 18, an abscissa denotes the volume ratio of the powders and an ordinate denotes the relative dielectric constant of the mixed substance 18.

As in Example 4, in FIG. 17, the relative dielectric constant of the sample was detected by reading a value of the relative dielectric constant when the volume ratio of the powders is 1.0.

Also, in FIG. 18, the relative dielectric constant of the sample was detected by reading a value of the relative dielectric constant when the volume ratio of the powders is 1.0.

The relative dielectric constant of the sample detected with respect to the liquid medium A by using the logarithmic mixture rule was 12.72, while the relative dielectric constant of the sample detected by using the Lichtenecker-Rother's Formula was 12.41. Thus, both relative dielectric constants had almost equal values mutually. Similarly, the relative dielectric constants of the samples were detected with respect to the liquid media B, C, D, E.

The relative dielectric constants of the samples detected with respect to the liquid media A, B, C, D, E are given in Table 3.

TABLE 3

|  | Logarithmic mixture rule | Lichtenecker-Rother's Formula |
|---|---|---|
| sample A | 12.723 | 12.405 |
| sample B | 12.886 | 12.456 |
| sample C | 12.837 | 11.776 |
| sample D | 12.144 | 8.6696 |
| sample E | 15.314 | 2.2302 |

As given in Table 3, the relative dielectric constants of the samples detected with respect to the liquid media A, B, C by using the logarithmic mixture rule and the Lichtenecker-Rother's Formula became almost equal mutually.

The relative dielectric constants of the liquid media were 0.93 times (liquid medium A), 1.28 times (liquid medium B), and 1.66 times (liquid medium C) the relative dielectric constant of the ceramic composition of the sample respectively. Thus, the relative dielectric constant of powders can be obtained with high precision when the relative dielectric constant of the mixed substance with respect to the ceramic composition of the sample ranges over 0.93 times to 1.66 times.

The present invention is not limited to above embodiments and Examples. It is needless to say that the present invention can be varied variously within a scope of the invention set forth in claims of this application and these variations are contained in the claims.

In the above embodiments and Examples, the $TM_{010}$ mode is used as the resonant mode when the resonant frequency is measured. For example, the $TM_{0m0}$ mode (m=2, 3, 4, . . . ) other than the $TM_{010}$ mode may be used as the resonant mode.

Also, in the above embodiments and Examples, the cavity resonator is formed cylindrically. But the cavity resonator may be formed as square, rectangle, triangle, or the like.

In addition, in the above embodiments, the ion-exchange water is used as the liquid medium. But either the liquid except the ion-exchange water or the mixed substance containing the liquid and the powder dielectric substance may be used as the liquid medium.

Also, in the above Examples, the mixed substance 18 injected into the tube 12 is fluidized by using the syringe 14a and the syringe 14b. But the mixed substance 18 may be fluidized by using the fluidizing apparatus 38A shown in FIG. 7.

In addition, in the above Examples, the mixed substance 18 injected into the tube 12 is fluidized by using the syringe 14a and the syringe 14b. But the mixed substance 18 may be fluidized by using the fluidizing apparatus 38A shown in FIG. 7.

Next, the cavity resonator used in the present invention will described with reference to FIGS. 19 to 21 hereunder.

The distribution of the electric field generated when the cavity resonator is shaped cylindrically will be explained with reference to FIG. 20 hereunder.

FIG. 20(a) shows the distribution of the electric field in the $TM_{010}$ mode in the ideal cylindrical cavity resonator, and the electric fields each indicated with an arrow are concentrated at a center portion of the cylinder.

Then, the dielectric substance as the measured object is placed at the maximum electric field point of the resonator.

It is desired that, as shown in FIG. 19(a), ideally the $TM_{010}$ mode cylindrical cavity resonator used in measurement of the relative dielectric constant of powders in the present invention should be formed as a closed cylinder.

However, actually it is impossible to take out the dielectric substance as the measured object from the closed cylinder. Therefore, as shown in FIG. 19(b), it is made possible by a structure in which an opening portion is provided to one of center portions of the resonator, to take out the dielectric substance as the measured object.

Meanwhile, as shown in FIG. 20(b), the electromagnetic wave leaks out from the inside of the resonator to the outside via the opening portion in the structure in which the opening portion is formed in the resonator, as shown in FIG. 19(b).

There existed the problem that measurement of the resonant frequency or the unloaded Q value becomes unstable due to the leakage of the electromagnetic wave, which has an influence upon measurement of the dielectric constant and the dielectric loss tangent.

In order to handle this problem, as shown in FIG. 19(c) (d), it is effective to provide a supporter on the outside of the opening portion.

FIG. 19(c) shows an example in which the supporter is provided on the outside of the opening portion when the opening portion is provided to one of the center portions of the resonator. FIG. 19(d) shows an example in which the supporter is provided on the outside of both opening portions when the opening portion is provided to both of the center portions of the resonator.

As shown in FIG. 19(c) (d), when the opening portion of the supporter portion is constructed sufficiently smaller than a diameter of the resonator, such supporter portion can act as a cut-off region.

A cut-off frequency of the supporter portion ($TM_{010}$ mode) is shown in FIG. 21.

It is appreciated from FIG. 21 that the cut-off frequency becomes higher when a length of the opening portion becomes shorter.

If a difference between the resonant frequency of the resonator and the cut-off frequency of the supporter portion is increased larger, the cut-off characteristic is excellent and therefore the leakage of the electromagnetic wave from the resonator can be suppressed.

A distribution of the electric field when the supporters are provided as shown in FIG. 19(d) is shown in FIG. 20(c).

A diameter is set to a length of the opening portion, as shown in FIG. 20(d), when the opening portion is circular. The longest portion of the opening portion is set to the length of the opening portion when the opening portion has a shape other than the circle.

Such mechanism makes it possible to prevent the leakage of the electromagnetic wave and get a cut-off structure, so that the resonant frequency and the unloaded Q value of the resonator can be measured stably.

Also, it is supposed easily that the better cut-off can be obtained as the length of the supporter becomes longer. Actually, it is difficult to get the optimum length of the supporter applied to get the cut-off. In some cases the unnecessarily long supporter is used.

Next, a simulation to detect the optimum value of the supporter in the cylindrical resonator will be explained hereunder.

FIG. 22 is a view showing conditions required for a resonator shape to execute the simulation to detect the optimum value of the supporter of the cylindrical cavity resonator.

Now, the resonant frequency is simulated by setting shapes of respective portions of the resonator and the dielectric constant of the dielectric substance, as shown in FIG. 22.

The results of the simulation are shown in FIG. 23.

It is appreciated from FIG. 23 that such a cut-off structure is obtained that the resonant frequency becomes constant within a range of h in excess of about 1.5 mm when the length of the supporter is changed.

Next, differences due to the relative dielectric constant $\in$ of the measured dielectric substance will be explained hereunder.

FIG. 24(a) is a graph showing raw data of the relationship between the length of the supporter and the resonant frequency when the relative dielectric constant of the dielectric substance is set to $\in=1$, $\in=100$, and $\in=500$ respectively, and FIG. 24(b) is a graph showing normalized data of the same.

It is seen from FIG. 24(b) that the cut-off structure can be obtained if h/d is in excess of 0.5.

Also, differences due to a height H of the resonator will be explained hereunder.

FIG. 25(a) is a graph showing raw data of a relationship between the length of the supporter and the resonant frequency when the height of the resonator is set to H=12.5 mm, H=25 mm, H=50 mm, H=100 mm, and H=140 mm respectively, and FIG. 25(b) is a graph showing normalized data of the same.

It is seen from FIG. 25(b) that the cut-off structure can be obtained if h/d is in excess of 0.5.

In addition, differences due to a diameter d of the insertion hole in the dielectric substance will be explained hereunder.

FIG. 26(a) is a graph showing raw data of a relationship between the length of the supporter and the resonant frequency when the diameter d of the insertion hole is set to d=1 mm, d=3 mm, and d=5 mm respectively, and FIG. 26(b) is a graph showing normalized data of the same.

It is seen from FIG. 26(b) that the cut-off structure can be obtained if h/d is in excess of 0.5.

In this case, the above simulation is applied to the resonator in FIG. 22. But results of the above simulation can be substantially applied to the case that the shape of the resonator and the shape of the opening portion are varied.

Also, the cavity resonator of the present invention is not limited to the application of the powders, and may be applied to any measured sample if such measured sample is formed of the dielectric substance.

The present invention is not limited to the foregoing embodiments and Examples. It is needless to say that the present invention can be varied variously within a scope of the invention set forth in claims of this application and these variations are contained in the claims.

In the above embodiments and Examples, in the measurement of the relative dielectric constant of the mixed substance 18, the relative dielectric constant of the mixed substance 18 is detected by inputting the electromagnetic wave into the cavity resonator and then measuring the resonant frequency based on the replied electromagnetic wave. For example, as disclosed in Patent Literature 1, the relative dielectric constant of the mixed substance may be detected by applying a voltage into a vessel in which a pair of electrodes are arranged and the mixed substance is filled.

Also, the relative dielectric constant of the mixed substance may be detected by inputting the electromagnetic wave into a rectangular waveguide and then measuring a transmission coefficient and a reflection coefficient of the replied electromagnetic wave.

Also, in above Examples, the $TM_{010}$ mode is used as the resonance mode applied when the resonant frequency is measured. The $TM_{0m0}$ mode (m=2, 3, 4, . . . ) other than the $TM_{010}$ mode may be used as the resonant mode.

Also, in the above embodiments and Examples, the relative dielectric constant of the liquid substance may be measured by using the measuring system 2.

Also, in the above embodiments and Examples, the cavity resonator is formed cylindrically. But the cavity resonator may be shaped into the square, the rectangle, the triangle, or the like.

In addition, in the above embodiments and Examples, the relative dielectric constant of the mixed substance is measured by changing the relative dielectric constant of the liquid substance in the situation that the volume ratio of the powders is kept constant. In case the relative dielectric constant of the mixed substance is measured by changing the relative dielectric constant of the liquid substance in the situation that the volume ratio of the powders is selected differently, the relative dielectric constant of the mixed substance 18 can be measured by using either the logarithmic mixture rule or Lichtenecker-Rother's Formula.

Also, in the above embodiments, the liquid such as water, alcohol, or the like or the mixed substance in which water, alcohol, and the like are mixed is employed as the liquid medium. But the liquid except the water or the alcohol, their mixed substance, or the mixed substance consisting of the liquid and the powder dielectric substance may be employed as the liquid medium.

In addition, in above Examples, the mixed substance 18 injected into the tube 12 is fluidized by using the syringe 14a and the syringe 14b. But the mixed substance 18 may be fluidized by using the fluidizing apparatus 38A shown in FIG. 7.

The $TM_{010}$ mode in the cavity resonator can be applied to a following system by utilizing the characteristics that the mode is the lowest mode (which has the lowest resonant frequency out of an infinite number of resonance peaks) and the electric filed are concentrated at a center axis of the cavity resonator.

The dielectric substance measuring system for inserting the rod-like-shaped dielectric substance into the electric-field concentrated portion on the center axis of the cavity resonator to which the supporter is provided, then measuring the resonant frequency and the unloaded Q value of the cavity resonator, and then measuring the relative dielectric constant and the dielectric loss tangent of the inserted rod-like dielectric substance based on the measured results can be implemented.

Since the $TM_{010}$ mode in the cavity resonator to which the supporter is provided is the lowest mode, the resonator or the filter that is excellent in the spurious characteristics can be implemented.

In this case, when the rod-like-shaped dielectric substance is inserted into the electric-field concentrated portion on the center axis of the cavity resonator to which the supporter is provided, the intended resonance characteristic can be attained.

What is claimed is:

1. A method of measuring a relative dielectric constant of powders comprising the steps of:
    calculating a relative dielectric constant of a mixed substance consisting of powders and a liquid medium; and
    calculating the relative dielectric constant of the mixed substance or a relative dielectric constant of the liquid medium as the relative dielectric constant of the powders where the relative dielectric constant of the mixed substance becomes equal to the relative dielectric constant of the liquid medium,
    wherein a procedure of detecting a point where the relative dielectric constant of the mixed substance becomes equal to the relative dielectric constant of the liquid medium is executed by measuring the relative dielectric constant of the mixed substance while changing gradually the relative dielectric constant of the liquid medium.

2. A method of measuring a relative dielectric constant of powders comprising the steps of:
    sealing a mixed substance consisting of the powders and a liquid medium in a resonator;
    inputting an electromagnetic wave into the resonator;
    calculating a relative dielectric constant of the mixed substance based on a response of the electromagnetic wave; and
    calculating a relative dielectric constant of the powders by determining where the relative dielectric constant of the mixed substance becomes equal to a relative dielectric constant of the liquid medium,
    wherein a procedure of detecting a point where the relative dielectric constant of the mixed substance becomes equal to the relative dielectric constant of the liquid medium is executed by measuring the relative dielectric constant of the mixed substance while changing gradually the relative dielectric constant of the liquid medium.

3. A method of measuring a relative dielectric constant of powders comprising the steps of:
    inputting an electromagnetic wave into a vessel in which a mixed substance consisting of the powders and a liquid medium is filled;
    calculating a relative dielectric constant of the mixed substance based on a response of the electromagnetic wave; and
    calculating a relative dielectric constant of the powders by determining where the relative dielectric constant of the mixed substance becomes equal to a relative dielectric constant of the liquid medium,
    wherein a procedure of detecting a point where the relative dielectric constant of the mixed substance becomes equal to the relative dielectric constant of the liquid medium is executed by measuring the relative dielectric constant of the mixed substance while changing gradually the relative dielectric constant of the liquid medium.

4. A method of measuring a relative dielectric constant of powders, according to any one of claims 1 to 3, wherein the liquid medium contains a plurality of liquids.

5. A method of measuring a relative dielectric constant of powders, according to any one of claims 1 to 3, wherein the liquid medium contains a liquid and a powder dielectric substance.

6. A method of measuring a relative dielectric constant of powders, according to any one of claims 1 to 3, wherein the liquid medium contains a liquid, a powder dielectric substance, and a dispersing agent.

* * * * *